US010640834B2

(12) United States Patent
Shimizu et al.

(10) Patent No.: US 10,640,834 B2
(45) Date of Patent: May 5, 2020

(54) METHOD FOR DETECTING MYCOPLASMA

(71) Applicants: NATIONAL UNIVERSITY CORPORATION TOKYO MEDICAL AND DENTAL UNIVERSITY, Tokyo (JP); LYMPHOTEC INC., Tokyo (JP)

(72) Inventors: Norio Shimizu, Tokyo (JP); Hideyuki Takahashi, Tokyo (JP)

(73) Assignees: National University Corporation Tokyo Medical and Dental University, Tokyo (JP); Lymphotec Inc., Tokyo (JP)

( * ) Notice: Subject to any disclaimer, the term of this patent is extended or adjusted under 35 U.S.C. 154(b) by 354 days.

(21) Appl. No.: 15/509,430

(22) PCT Filed: Sep. 7, 2015

(86) PCT No.: PCT/JP2015/004535
§ 371 (c)(1),
(2) Date: Mar. 7, 2017

(87) PCT Pub. No.: WO2016/038877
PCT Pub. Date: Mar. 17, 2016

(65) Prior Publication Data
US 2017/0240959 A1 Aug. 24, 2017

(30) Foreign Application Priority Data

Sep. 10, 2014 (JP) .................. 2014-184379

(51) Int. Cl.
*C12Q 1/689* (2018.01)
*C12Q 1/68* (2018.01)
*C12N 15/09* (2006.01)

(52) U.S. Cl.
CPC ............. *C12Q 1/689* (2013.01); *C12N 15/09* (2013.01); *C12Q 1/68* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 2004/0176584 A1 | 9/2004 | Terlesky |
| 2007/0065828 A1 | 3/2007 | Kim et al. |
| 2011/0104686 A1 | 5/2011 | Litterst et al. |
| 2013/0023443 A1 | 1/2013 | Shirai et al. |

FOREIGN PATENT DOCUMENTS

| JP | 1992-004899 A | 1/1992 |
| JP | 1993-05-000088 A | 1/1993 |
| JP | 1994-098800 A | 4/1994 |
| JP | 2004-305207 A | 11/2004 |
| JP | 2012-60925 A | 3/2012 |
| JP | 2013-515458 A | 5/2013 |
| KR | 10-2009-0081039 | 7/2009 |
| WO | 2005/078102 | 8/2005 |
| WO | 2009/093856 | 7/2009 |
| WO | 2011/122034 | 10/2011 |
| WO | 2013/176136 | 11/2013 |

OTHER PUBLICATIONS

Stormer et al., "Broad-range real-time PCR assay for the rapid identification of cell-line contaminants and clinically important mollicute species", International Journal of Medical Microbiology, Apr. 1, 2009, vol. 299, Issue 4, pp. 291-300.

Harasawa et al., "Detection and tentative identification of dominant *Mycoplasma* species in cell cultures by restriction analysis of the 16S-23S rRNA intergenic spacer regions", Re. Microbiol., 1993, vol. 443, pp. 489-493.

Stakenborg, et al., "A multiplex PCR to identify porcine *Mycoplasmas* present in broth cultures", Vet. Res. Commun., vol. 30, Issue 3, Apr. 30, 2006, pp. 239-243.

Fraga et al., "A multiplex real-time PCR for detection of *Mycoplasma gallisepticum* and *Mycoplasma synoviae* in clinical samples from Brazilian commercial poultry flocks", Braz. J. Microbiol., Oct. 30, 2013, vol. 44, No. 2, p. 505-510.

(Continued)

*Primary Examiner* — Samuel C Woolwine
(74) *Attorney, Agent, or Firm* — Occhiuti & Rohlicek LLP

(57) ABSTRACT

An object of the present invention is to provide a detection method for *Mycoplasma* by which a greater number of *Mycoplasma* species can be more quickly and easily detected with high sensitivity and accuracy, a set of a forward primer, a reverse primer and a probe for the detection and a kit containing the set. *Mycoplasma* in a test sample is detected by a multiplex real time quantitative PCR using one or more forward primers, each of which is an oligonucleotide consisting of a nucleotide sequence, which is selected from the group consisting of nucleotide sequences each consisting of continuous 17 to 30 nucleotides in the nucleotide sequence represented by SEQ ID No: 1, and which contains a nucleotide sequence at nucleotide positions 14 to 24 in SEQ ID No: 1; reverse primers, each of which is an oligonucleotide consisting of a nucleotide sequence, which is selected from the group consisting of nucleotide sequences each consisting of continuous 17 to 26 nucleotides in the one or more nucleotide sequences represented by SEQ ID Nos: 14 and 17 to 20; and a probe(s), which is an oligonucleotide, which consists of a nucleotide sequence selected from the group consisting of nucleotide sequences each consisting of continuous 17 to 26 nucleotides in the nucleotide sequence represented by SEQ ID No: 33, or which consists of a complementary nucleotide sequence thereto.

14 Claims, 9 Drawing Sheets

Specification includes a Sequence Listing.

(56) References Cited

OTHER PUBLICATIONS

Takahashi et al., "Development of new *Mycoplasma* laboratory procedure by multiplex qPCR", Regemerative Therapy, vol. 13, 2014, p. 357.

Frech, Christian, Karin Breuer, Bernhard Ronacher, Thomas Kern, Christof Sohn, and Gerhard Gebauer. "hybseek: Pathogen primer design tool for diagnostic multi-analyte assays." computer methods and programs in biomedicine 94, No. 2 (2009): 152-160.

Fraga, Aline Padilha, Tatiana de Vargas, Nilo Ikuta, André Salvador Kazantzi Fonseca, Álvaro José Celmer, Edmundo Kanan Marques, and Vagner Ricardo Lunge. "A Multiplex real-time PCR for detection of *Mycoplasma gallisepticum* and *Mycoplasma synoviae* in clinical samples from Brazilian commercial poultry flocks." Brazilian Journal of Microbiology 44, No. 2 (2013): 505-510.

Stakenborg, Tim, Jo Vicca, Patrick Butaye, H. Imberechts, Johan Peeters, Aart De Kruif, Freddy Haesebrouck, and Dominique Maes. "A multiplex PCR to identify porcine *Mycoplasmas* present in broth cultures." Veterinary research communications 30, No. 3 (2006): 239-247.

[Figure 1]

|  | 16s Ribosome gene | Spacer region | 23s Ribosome gene | Amplicon size (bp) |
|---|---|---|---|---|
| Group 1a | F1 → | P1-1, P1-3 ————▶ | ◀———— R4-1 | 267-320 |
| Group 1b | F1 → | P1-1, P1-3 ————▶ | ◀———— R4-2 | 384-398 |
| Group 1c | F1 → | P1-1 ————▶ | ◀———— R4-3 | 345 |
| Group 2 | F1 → | P1-4 ————▶ | ◀———— R1 | 286-319 |
| Group 3a | F1 → | P1-1 ————▶ | ◀———— R3 | 184 |
| Group 3b | F1 → | P1-2 ————▶ | ◀———— R6 | 169 |
| Group 4 | F1 → | P1-1 ————▶ | ◀———— R2 | 99 |
| Group 5 | F2 → | P2 ————▶ | ◀———— R5 | 112 |
| Group 6 | F1 → | P1-3 ————▶ | ◀———— R7 | 159 |

Representative Example of each group
Group 1a: M. orale, Group 1b: M. fermentans, Group 1c: M. hyorhinis,
Group 2: M. pneumoniae, Group 3a: M. gallisepticum, Group 3b: U. urealyticum,
Group 4: A. laidlawii, Group 5: S. citri, Group 6: M. synoviae

| | Forward primer | Probe | Reverse primer | Mollicutes species |
|---|---|---|---|---|
| Group 1a | F1 | P1-1, P1-3 | R4-1 | M. arginini, M. buccale, M. faucium, M. hominis, M. orale, M. salivarium |
| Group 1b | F1 | P1-1, P1-3 | R4-2 | M. fermentans, M. lipophilum, M. primatum |
| Group 1c | F1 | P1-1 | R4-3 | M. hyorhinis |
| Group 2 | F1 | P1-4 | R1 | M. genitalium, M. pneumoniae |
| Group 3a | F1 | P1-1 | R3 | M. gallisepticum |
| Group 3b | F1 | P1-2 | R6 | U. urealyticum |
| Group 4 | F1 | P1-1 | R2 | A. laidlawii |
| Group 5 | F2 | P2 | R5 | S. citri |
| Group 6 | F1 | P1-3 | R7 | M. synoviae |

[Figure 2]

| | cfu/reaction | Detection method of invention | Detection method of reference document |
|---|---|---|---|
| Mycoplasma arginini | 1000 | 3/3 | 3/3 |
| | 100 | 3/3 | 3/3 |
| | 10 | 3/3 | 3/3 |
| | 5 | 3/3 | 3/3 |
| Mycoplasma fermentans | 1000 | 3/3 | 3/3 |
| | 100 | 3/3 | 3/3 |
| | 10 | 3/3 | 3/3 |
| | 5 | 3/3 | 0/3 |
| Mycoplasma gallisepticum | 1000 | 3/3 | 0/3 (3/3 only for 10^5) |
| | 100 | 3/3 | 0/3 |
| | 10 | 3/3 | 0/3 |
| | 5 | 3/3 | 0/3 |
| Mycoplasma hyorhinis | 1000 | 3/3 | 3/3 |
| | 100 | 3/3 | 3/3 |
| | 10 | 3/3 | 3/3 |
| | 5 | 3/3 | 3/3 |
| Mycoplasma orale | 1000 | 3/3 | 3/3 |
| | 100 | 3/3 | 3/3 |
| | 10 | 3/3 | 0/3 |
| | 5 | 3/3 | 0/3 |
| Mycoplasma pneumoniae | 1000 | 3/3 | 3/3 |
| | 100 | 3/3 | 3/3 |
| | 10 | 3/3 | 3/3 |
| | 5 | 3/3 | 3/3 |
| Mycoplasma synoviae | 1000 | 3/3 | 3/3 |
| | 100 | 3/3 | 3/3 |
| | 10 | 3/3 | 1/3 |
| | 5 | 3/3 | 0/3 |
| Acholeplasma laidlawii | 1000 | 3/3 | 0/3 (3/3 only for 10^5) |
| | 100 | 3/3 | 0/3 |
| | 10 | 3/3 | 0/3 |
| | 5 | 3/3 | 0/3 |
| Spiroplasma citri | 1000 | 3/3 | 0/3 |
| | 100 | 3/3 | 0/3 |
| | 10 | 3/3 | 0/3 |
| | 5 | 3/3 | 0/3 |

[Figure 3]

| Bacterial genome DNA | | Fungal genome DNA | Mammal cells |
|---|---|---|---|
| Bacteroides vulgatus | Propionibacterium acnes | Aspergillus niger | Human T lymphocyte |
| Bacillus subtilis | Salmonella enterica subsp. enterica | Candida albicans | Mouse T lymphocyte |
| Brevibacillus brevis | Staphylococcus aureus | | Raji cell |
| Clostridium acetobutylicum | Staphylococcus epidermidis | | CHO DG44 |
| Clostridium kluyveri | Streptococcus mutans | | |
| Clostridium sporogenes | Streptococcus pneumoniae | | |
| Escherichia coli | Streptococcus bovis | | |
| Enterococcus faecalis | Streptomyces avermitilis | | |
| Gluconacetobacter xylinus | Rhodococcus erythropolis | | |
| Klebsiella pneumoniae | Rothia dentocariosa | | |
| Lactobacillus acidophilus | Tetragenococcus halophilus | | |
| Lactobacillus delbrueckii subsp. bulgaricus | | | |
| Lactobacillus casei | | | |
| Lactobacillus gasseri | | | |
| Pseudomonas aeruginosa | | | |

Bacteria, fungi and mammal-derived cells which did not show cross reactivity by Multiplex qPCR

[Figure 4]

```
                                                                    Degree of
                                                                    positional
Forward primer            F1 primer              Probe                 shift
    F1      TGATTGGAGTTAAGTCGTAACAAGGTACCCCTACGAGAACGTGGGRTGGATYACCTCCTTTCAAA    0

M1 primer              Probe
    M1      TGATTGGAGTTAAGTCGTAACAAGGTACCCCTACGAGAACGTGGGRTGGATYACCTCCTTTCAAA   +1

TF primer              Probe
    TF      TGATTGGAGTTAAGTCGTAACAAGGTACCCCTACGAGAACGTGGGRTGGATYACCTCCTTTCAAA   -2

MyTF-1 primer           Probe
  MyTF-1    TGATTGGAGTTAAGTCGTAACAAGGTACCCCTACGAGAACGTGGGRTGGATYACCTCCTTTCAAA   +2

MyTF-2 primer               Probe
  MyTF-2    TGATTGGAGTTAAGTCGTAACAAGGTACCCCTACGAGAACGTGGGRTGGATYACCTCCTTTCAAA   -8

MyTF-3 primer              Probe
  MyTF-3    TGATTGGAGTTAAGTCGTAACAAGGTACCCCTACGAGAACGTGGGRTGGATYACCTCCTTTCAAA   -5

MyTF-4 primer           Probe
  MyTF-4    TGATTGGAGTTAAGTCGTAACAAGGTACCCCTACGAGAACGTGGGRTGGATYACCTCCTTTCAAA   -7

MyTF-5 primer          Probe
  MyTF-5    TGATTGGAGTTAAGTCGTAACAAGGTACCCCTACGAGAACGTGGGRTGGATYACCTCCTTTCAAA   -4

MyTF-6 primer          Probe
  MyTF-6    TGATTGGAGTTAAGTCGTAACAAGGTACCCCTACGAGAACGTGGGRTGGATYACCTCCTTTCAAA   -1

Degree of
                                                                    positional
Reverse primer    Probe                           R1 primer            shift
    R1      ACGTGGGRTGGATYACCTCCTTTCAAATGGAG--//--GGGCTTATGGTGGATGCCTTGGCACTAA   0

Probe                           M6-2 primer
   M6-2     ACGTGGGRTGGATYACCTCCTTTCAAATGGAG--//--GGGCTTATGGTGGATGCCTTGGCACTAA  -1

Probe                           TR primer
    TR      ACGTGGGRTGGATYACCTCCTTTCAAATGGAG--//--GGGCTTATGGTGGATGCCTTGGCACTAA  -5

Probe                           TR-2 primer
   TR-2     ACGTGGGRTGGATYACCTCCTTTCAAATGGAG--//--GGGCTTATGGTGGATGCCTTGGCACTAA  -3
```

[Figure 5]

| | cfu/tube | F1 ||| M1 ||| TF ||| MyTF-1 |||
|---|---|---|---|---|---|---|---|---|---|---|---|---|---|
| | | M6-2 | TR | TR-2 | M6-2 | TR | TR-2 | M6-2 | TR | TR-2 | M6-2 | TR | TR-2 |
| | | ct value | ct value | R1 ct value | ct value | ct value | R1 ct value | ct value | ct value | R1 ct value | ct value | ct value | R1 ct value |
| 1 M. genitalium | about 10^6 | 27.07 | 26.18 | 26.71 | 27.24 | 31.68 | 32.34 | 30.58 | 31.58 | 29.00 | 29.70 | 28.64 | 30.45 | 27.80 | 27.87 | 27.84 | 26.80 |
| 2 L. bulgaricus | about 10^6 | - | - | - | - | - | - | - | - | - | - |
| 3 DW | | - | - | - | - | - | - | - | - | - | - |

(Note: row structure — columns: cfu/tube, then for each primer set (F1, M1, TF, MyTF-1) three sub-columns M6-2, TR, TR-2 with ct value)

| | cfu/tube | MyTF-2 ||| MyTF-3 ||| MyTF-4 ||| MyTF-5 |||
|---|---|---|---|---|---|---|---|---|---|---|---|---|
| | | M6-2 | TR | TR-2 | M6-2 | TR | TR-2 | M6-2 | TR | TR-2 | M6-2 | TR | TR-2 |
| | | ct value | ct value | R1 ct value | ct value | ct value | R1 ct value | ct value | ct value | R1 ct value | ct value | ct value | R1 ct value |
| 1 M. genitalium | about 10^6 | 25.31 | 25.76 | 25.49 | 25.31 | 25.80 | 25.19 | 25.90 | 26.91 | 25.12 | 25.58 | 25.72 | 27.84 | 25.08 | 25.28 | 25.68 | 25.52 |
| 2 L. bulgaricus | about 10^6 | - | *41.95 | *33.49 | *21.40 | - | - | *25.50 | - | - | *39.90 | - | - | - | - |
| 3 DW | | - | - | - | - | - | - | - | - | - | - | - | - |

| | cfu/tube | MyTF-6 |||
|---|---|---|---|---|
| | | M6-2 | TR | TR-2 |
| | | ct value | ct value | R1 ct value |
| 1 M. genitalium | about 10^6 | 25.52 | 23.81 | 25.51 | 26.10 |
| 2 L. bulgaricus | about 10^6 | - | *42.25 | - | - |
| 3 DW | | - | - | - | - |

* indicates the case where L. bulgaricus was detected

SEQUENCE LISTING

```
<160> NUMBER OF SEQ ID NOS: 48

<210> SEQ ID NO 1
<211> LENGTH: 30
<212> TYPE: DNA
<213> ORGANISM: Artificial
<220> FEATURE:
<223> OTHER INFORMATION: Forward primer of the present invention
<220> FEATURE:
<223> OTHER INFORMATION: Inventor: SHIMIZU, Norio; TAKAHASHI, Hideyuki

<400> SEQUENCE: 1
agttaagtcg taacaaggta tccstacgag                                         30

<210> SEQ ID NO 2
<211> LENGTH: 30
<212> TYPE: DNA
<213> ORGANISM: Artificial
<220> FEATURE:
<223> OTHER INFORMATION: F1-family-Forward primer

<400> SEQUENCE: 2
agttaagtcg taacaaggta tccctacgag                                         30

<210> SEQ ID NO 3
<211> LENGTH: 30
<212> TYPE: DNA
<213> ORGANISM: Artificial
<220> FEATURE:
<223> OTHER INFORMATION: F2-family-Forward primer

<400> SEQUENCE: 3
```

-continued agttaagtcg taacaaggta tccgtacgag                                    30

<210> SEQ ID NO 4
<211> LENGTH: 19
<212> TYPE: DNA
<213> ORGANISM: Artificial
<220> FEATURE:
<223> OTHER INFORMATION: F1-Forward primer

<400> SEQUENCE: 4
gtaacaaggt atccctacg                                                19

<210> SEQ ID NO 5
<211> LENGTH: 19
<212> TYPE: DNA
<213> ORGANISM: Artificial
<220> FEATURE:
<223> OTHER INFORMATION: M1-Forward primer

<400> SEQUENCE: 5
taacaaggta tccctacga                                                19

<210> SEQ ID NO 6
<211> LENGTH: 19
<212> TYPE: DNA
<213> ORGANISM: Artificial
<220> FEATURE:
<223> OTHER INFORMATION: TF-Forward primer

<400> SEQUENCE: 6
tcgtaacaag gtatcccta                                                19

<210> SEQ ID NO 7
<211> LENGTH: 20
<212> TYPE: DNA
<213> ORGANISM: Artificial
<220> FEATURE:
<223> OTHER INFORMATION: MyTF-1-Forward primer

<400> SEQUENCE: 7
taacaaggta tccctacgag                                               20

<210> SEQ ID NO 8
<211> LENGTH: 21
<212> TYPE: DNA
<213> ORGANISM: Artificial
<220> FEATURE:
<223> OTHER INFORMATION: MyTF-2-Forward primer

<400> SEQUENCE: 8
gagttaagtc gtaacaaggt a                                             21

<210> SEQ ID NO 9
<211> LENGTH: 22
<212> TYPE: DNA
<213> ORGANISM: Artificial
<220> FEATURE:
<223> OTHER INFORMATION: MyTF-3-Forward primer

<400> SEQUENCE: 9
gttaagtcgt aacaaggtat cc                                            22

<210> SEQ ID NO 10
<211> LENGTH: 22
<212> TYPE: DNA
<213> ORGANISM: Artificial

```
<220> FEATURE:
<223> OTHER INFORMATION: MyTF-4-Forward primer

<400> SEQUENCE: 10
gagttaagtc gtaacaaggt at                                          22

<210> SEQ ID NO 11
<211> LENGTH: 19
<212> TYPE: DNA
<213> ORGANISM: Artificial
<220> FEATURE:
<223> OTHER INFORMATION: MyTF-5-Forward primer

<400> SEQUENCE: 11
agtcgtaaca aggtatccc                                              19

<210> SEQ ID NO 12
<211> LENGTH: 21
<212> TYPE: DNA
<213> ORGANISM: Artificial
<220> FEATURE:
<223> OTHER INFORMATION: MyTF-6-Forward primer

<400> SEQUENCE: 12
gtcgtaacaa ggtatcccta c                                           21

<210> SEQ ID NO 13
<211> LENGTH: 19
<212> TYPE: DNA
<213> ORGANISM: Artificial
<220> FEATURE:
<223> OTHER INFORMATION: F2-Forward primer

<400> SEQUENCE: 13
gtaacaaggt atccgtacg                                              19

<210> SEQ ID NO 14
<211> LENGTH: 26
<212> TYPE: DNA
<213> ORGANISM: Artificial
<220> FEATURE:
<223> OTHER INFORMATION: Reverse primer of the present
      invention-R1andR4-family

<400> SEQUENCE: 14
agwsccaagg catccaccah awrctc                                      26

<210> SEQ ID NO 15
<211> LENGTH: 26
<212> TYPE: DNA
<213> ORGANISM: Artificial
<220> FEATURE:
<223> OTHER INFORMATION: R1-family-Reverse primer

<400> SEQUENCE: 15
agtgccaagg catccaccat aagctc                                      26

<210> SEQ ID NO 16
<211> LENGTH: 26
<212> TYPE: DNA
<213> ORGANISM: Artificial
<220> FEATURE:
<223> OTHER INFORMATION: R4-family-Reverse primer

<400> SEQUENCE: 16
agacccaagg catccaccam awactc                                      26
```

<210> SEQ ID NO 17
<211> LENGTH: 26
<212> TYPE: DNA
<213> ORGANISM: Artificial
<220> FEATURE:
<223> OTHER INFORMATION: R2-Reverse primer

<400> SEQUENCE: 17
actacttact agtagtcatc ttgtgc                                       26

<210> SEQ ID NO 18
<211> LENGTH: 24
<212> TYPE: DNA
<213> ORGANISM: Artificial
<220> FEATURE:
<223> OTHER INFORMATION: R3-R6-Reverse primer

<400> SEQUENCE: 18
tsaraactra atagaatccg acca                                         24

<210> SEQ ID NO 19
<211> LENGTH: 25
<212> TYPE: DNA
<213> ORGANISM: Artificial
<220> FEATURE:
<223> OTHER INFORMATION: R5-Reverse primer

<400> SEQUENCE: 19
tctctgaaaa ctaaacataa cggtc                                        25

<210> SEQ ID NO 20
<211> LENGTH: 23
<212> TYPE: DNA
<213> ORGANISM: Artificial
<220> FEATURE:
<223> OTHER INFORMATION: R7-Reverse primer

<400> SEQUENCE: 20
aactaaatac aatagcccaa ggc                                          23

<210> SEQ ID NO 21
<211> LENGTH: 23
<212> TYPE: DNA
<213> ORGANISM: Artificial
<220> FEATURE:
<223> OTHER INFORMATION: R1-Reverse primer

<400> SEQUENCE: 21
agtgccaagg catccaccat aag                                          23

<210> SEQ ID NO 22
<211> LENGTH: 22
<212> TYPE: DNA
<213> ORGANISM: Artificial
<220> FEATURE:
<223> OTHER INFORMATION: M6-2-Reverse primer

<400> SEQUENCE: 22
agtgccaagg catccaccat aa                                           22

<210> SEQ ID NO 23
<211> LENGTH: 18
<212> TYPE: DNA
<213> ORGANISM: Artificial
<220> FEATURE:

```
<223> OTHER INFORMATION: TR-Reverse primer

<400> SEQUENCE: 23
agtgccaagg catccacc                                                      18

<210> SEQ ID NO 24
<211> LENGTH: 18
<212> TYPE: DNA
<213> ORGANISM: Artificial
<220> FEATURE:
<223> OTHER INFORMATION: TR-2-Reverse primer

<400> SEQUENCE: 24
tgccaaggca tccaccat                                                      18

<210> SEQ ID NO 25
<211> LENGTH: 24
<212> TYPE: DNA
<213> ORGANISM: Artificial
<220> FEATURE:
<223> OTHER INFORMATION: R4-1-Reverse primer

<400> SEQUENCE: 25
acccaaggca tccaccaaaa actc                                               24

<210> SEQ ID NO 26
<211> LENGTH: 24
<212> TYPE: DNA
<213> ORGANISM: Artificial
<220> FEATURE:
<223> OTHER INFORMATION: R4-2-Reverse primer

<400> SEQUENCE: 26
acccaaggca tccaccacaa actc                                               24

<210> SEQ ID NO 27
<211> LENGTH: 24
<212> TYPE: DNA
<213> ORGANISM: Artificial
<220> FEATURE:
<223> OTHER INFORMATION: R4-3-Reverse primer

<400> SEQUENCE: 27
acccaaggca tccaccaaat actc                                               24

<210> SEQ ID NO 28
<211> LENGTH: 20
<212> TYPE: DNA
<213> ORGANISM: Artificial
<220> FEATURE:
<223> OTHER INFORMATION: R3-Reverse primer

<400> SEQUENCE: 28
aactgaatag aatccgacca                                                    20

<210> SEQ ID NO 29
<211> LENGTH: 20
<212> TYPE: DNA
<213> ORGANISM: Artificial
<220> FEATURE:
<223> OTHER INFORMATION: R6-Reverse primer

<400> SEQUENCE: 29
aactaaatag aatccgacca                                                    20
```

```
<210> SEQ ID NO 30
<211> LENGTH: 4
<212> TYPE: DNA
<213> ORGANISM: Artificial
<220> FEATURE:
<223> OTHER INFORMATION: 4 nucleotides of the core of the reverse
      primer-1

<400> SEQUENCE: 30 aaaa                                                                      4

<210> SEQ ID NO 31
<211> LENGTH: 4
<212> TYPE: DNA
<213> ORGANISM: Artificial
<220> FEATURE:
<223> OTHER INFORMATION: 4 nucleotides of the core of the reverse
      primer-2

<400> SEQUENCE: 31 caaa                                                                      4

<210> SEQ ID NO 32
<211> LENGTH: 4
<212> TYPE: DNA
<213> ORGANISM: Artificial
<220> FEATURE:
<223> OTHER INFORMATION: 4 nucleotides of the core of the reverse
      primer-3

<400> SEQUENCE: 32 aata                                                                      4

<210> SEQ ID NO 33
<211> LENGTH: 26
<212> TYPE: DNA
<213> ORGANISM: Artificial
<220> FEATURE:
<223> OTHER INFORMATION: P1-P2-Probe

<400> SEQUENCE: 33
aacgtgsggr tggatyacct cctttc                                             26

<210> SEQ ID NO 34
<211> LENGTH: 26
<212> TYPE: DNA
<213> ORGANISM: Artificial
<220> FEATURE:
<223> OTHER INFORMATION: P1-1-family-Probe

<400> SEQUENCE: 34
aacgtgggga tggatcacct cctttc                                             26

<210> SEQ ID NO 35
<211> LENGTH: 26
<212> TYPE: DNA
<213> ORGANISM: Artificial
<220> FEATURE:
<223> OTHER INFORMATION: P1-2-family-Probe

<400> SEQUENCE: 35 aacgtgggggg tggattacct cctttc                                            26

<210> SEQ ID NO 36
<211> LENGTH: 26
<212> TYPE: DNA
<213> ORGANISM: Artificial
```

```
<220> FEATURE:
<223> OTHER INFORMATION: P1-3-family-Probe

<400> SEQUENCE: 36
aacgtgggga tggattacct cctttc                                      26

<210> SEQ ID NO 37
<211> LENGTH: 26
<212> TYPE: DNA
<213> ORGANISM: Artificial
<220> FEATURE:
<223> OTHER INFORMATION: P1-4-family-Probe

<400> SEQUENCE: 37
aacgtggggg tggatcacct cctttc                                      26

<210> SEQ ID NO 38
<211> LENGTH: 26
<212> TYPE: DNA
<213> ORGANISM: Artificial
<220> FEATURE:
<223> OTHER INFORMATION: P2-family-Probe

<400> SEQUENCE: 38
aacgtgcgga tggatcacct cctttc                                      26

<210> SEQ ID NO 39
<211> LENGTH: 22
<212> TYPE: DNA
<213> ORGANISM: Artificial
<220> FEATURE:
<223> OTHER INFORMATION: P1-1-Probe

<400> SEQUENCE: 39
acgtggggat ggatcacctc ct                                          22

<210> SEQ ID NO 40
<211> LENGTH: 22
<212> TYPE: DNA
<213> ORGANISM: Artificial
<220> FEATURE:
<223> OTHER INFORMATION: P1-2-Probe

<400> SEQUENCE: 40 acgtggggt ggattacctc ct                                           22

<210> SEQ ID NO 41
<211> LENGTH: 22
<212> TYPE: DNA
<213> ORGANISM: Artificial
<220> FEATURE:
<223> OTHER INFORMATION: P1-3-Probe

<400> SEQUENCE: 41
acgtggggat ggattacctc ct                                          22

<210> SEQ ID NO 42
<211> LENGTH: 22
<212> TYPE: DNA
<213> ORGANISM: Artificial
<220> FEATURE:
<223> OTHER INFORMATION: P1-4-Probe

<400> SEQUENCE: 42
acgtgggggt ggatcacctc ct                                          22
```

```
<210> SEQ ID NO 43
<211> LENGTH: 22
<212> TYPE: DNA
<213> ORGANISM: Artificial
<220> FEATURE:
<223> OTHER INFORMATION: P2-Probe

<400> SEQUENCE: 43
acgtgcggat ggatcacctc ct                                              22

<210> SEQ ID NO 44
<211> LENGTH: 10
<212> TYPE: DNA
<213> ORGANISM: Artificial
<220> FEATURE:
<223> OTHER INFORMATION: Core of P1-1-probe

<400> SEQUENCE: 44
gggatggatc                                                            10

<210> SEQ ID NO 45
<211> LENGTH: 10
<212> TYPE: DNA
<213> ORGANISM: Artificial
<220> FEATURE:
<223> OTHER INFORMATION: Core of P1-2-probe

<400> SEQUENCE: 45
ggggtggatt                                                            10

<210> SEQ ID NO 46
<211> LENGTH: 10
<212> TYPE: DNA
<213> ORGANISM: Artificial
<220> FEATURE:
<223> OTHER INFORMATION: Core of P1-3-probe

<400> SEQUENCE: 46
gggatggatt                                                            10

<210> SEQ ID NO 47
<211> LENGTH: 10
<212> TYPE: DNA
<213> ORGANISM: Artificial
<220> FEATURE:
<223> OTHER INFORMATION: Core of P1-4-probe

<400> SEQUENCE: 47
ggggtggatc                                                            10

<210> SEQ ID NO 48
<211> LENGTH: 10
<212> TYPE: DNA
<213> ORGANISM: Artificial
<220> FEATURE:
<223> OTHER INFORMATION: Core of P2-probe

<400> SEQUENCE: 48
cggatggatc                                                            10
```

METHOD FOR DETECTING MYCOPLASMA

CROSS REFERENCE TO RELATED APPLICATIONS

This application is a National Stage of International Application No. PCT/JP2015/004535 filed on Sep. 7, 2015, which claims priority to Japanese Application No. 2014-184379 filed on Sep. 10, 2014, the contents of which are hereby incorporated by reference in their entirety.

TECHNICAL FIELD

The present invention relates to a method for detecting *Mycoplasma*, and particularly relates to a *Mycoplasma* detection method by which a greater number of *Mycoplasma* species can be more quickly and easily detected with high sensitivity and accuracy, a set of a forward primer, a reverse primer and a probe, and a kit containing such a set.

BACKGROUND ART

*Mycoplasma* is a *eubacterium* classified in the class Mollicutes. In a broad sense, not only the genus *Mycoplasma* but also the genus *Ureaplasma*, the genus *Mesoplasma*, the genus *Entomoplasma*, the genus *Spiroplasma*, the genus *Acholeplasma*, the genus *Asteroleplasma*, and the genus *Thermoplasma* are sometimes called *Mycoplasma*. *Mycoplasma* is the smallest self-replicable organism. At least 200 types of species are presently known. *Mycoplasma* has no peptidoglycan cell wall, which is commonly found in eubacteria. Because of this, the cell has an indefinite shape and flexibility. Since *Mycoplasma* has a small size of about 0.2 to 0.8 μm and indefinite in shape, the cell can pass through a sterilization filter of about 0.2 μm. Because of this, even if a cell culture medium is subjected to filter sterilization, *Mycoplasma* cannot be removed. In particular, certain species of *Mycoplasma* are known as representative bacteria causing microbial contamination in cell culture.

Due to the absence of a cell wall, *Mycoplasma* is not sensitive to antibiotics such as penicillin-based and cephem-based antibiotics, usually used in cell culture. Unlike other bacterial contaminants, *Mycoplasma* proliferates in a cell culture supernatant without causing visible changes such as a turbidity increase of medium and degeneration of cultured cell. Thus, *Mycoplasma* contamination is overlooked and spread unless *Mycoplasma* is found by the *Mycoplasma* detection method. *Mycoplasma* adsorbs to the cell membrane and depletes cell nutrients, thereby inhibiting cell proliferation and changing gene expression. For the reasons, experimental results from an infected culture are low in reliability. Accordingly, it is an important prerequisite to check the absence of *Mycoplasma* contamination before study. If cells infected with *Mycoplasma* are used for treatment in the field of regenerative medicine and cell therapy requiring cell culture, the cells negatively affect the immune system and may have a risk of causing pneumonia, urethritis and arthritis. Accordingly, it is essential to carry out a *Mycoplasma* test in production sites of biological material-derived medicines and clinical sites of regenerative medicine and cell therapy.

As the *Mycoplasma* test method, the Japanese pharmacopoeia proposes three methods, i.e., a culture method (agar and liquid medium method), a DNA staining method using indicator cells (indicator cell culture method) and a Nested PCR method, as reference information. However, the culture method has a problem in that a culture period of 28 days is too long. The DNA staining method has a problem in that the sensitivity is low. The Nested PCR method has a problem in that a false-positive due to carry over contamination of an amplified product is likely to occur. The three test methods are all insufficient as a safety test method for regenerative medicine and cell therapy used in practice. In the circumstances, a more practical method for detecting *Mycoplasma* has been in developing.

For example, Patent Document 1 discloses e.g., a primer pair for use in specifically amplifying a gene of *Mycoplasma* by real time PCR and a method for detecting *Mycoplasma* using the primer pair. In this method, 23S rRNA gene of *Mycoplasma* is used as an amplification target. Non-Patent Document 1 discloses e.g., a primer pair for use in specifically amplifying a gene of e.g., *Mycoplasma*, by real time PCR, a probe for detecting a product amplified by use of the primer pair and a method for detecting e.g., *Mycoplasma* by the primer pair and probe. In this method, tuf gene of e.g., *Mycoplasma* is used as an amplification target. Patent Document 2 discloses e.g., a primer set for use in specifically amplifying a *Mycoplasma* gene by a special gene amplification method called LAMP (loop-mediated isothermal amplification) method, a probe for detecting a product amplified by use of the primer set and a method for detecting *Mycoplasma* using the primer set and probe. In this method, 16S rRNA gene of *Mycoplasma* is used as an amplification target. Patent Document 3 discloses e.g., a kit containing a primer for use in specifically amplifying a gene of *Mycoplasma* by a real time nucleic acid amplification reaction (real time PCR) and a method for detecting *Mycoplasma* in a cell culture medium by use of the primer. In this method, rpoB gene of *Mycoplasma* is used as an amplification target. Likewise, a method for detecting *Mycoplasma* has been in developing. In the circumstance, a more practical *Mycoplasma* detection method by which a greater number of *Mycoplasma* species can be more quickly and easily detected with high sensitivity and accuracy has been desired.

Note that, Non-Patent Document 2 discloses that primers, which are used in a conventional Nested PCR method for detecting *Mycoplasma*, are used as primers for targeting 16S rRNA gene, 23S rRNA gene of *Mycoplasma* and the spacer region between both genes, for amplification. However, the conventional Nested PCR has a problem in that a false positive due to carry over contamination with an amplified product is likely to occur, as mentioned above.

In the meantime, certain species of *Mycoplasma* are known to cause pneumonia. For example, Patent Document 4 discloses e.g., a method for detecting a pneumococcus such as *Mycoplasma pneumoniae* by specifically amplifying a gene of the pneumococcus by e.g., PCR, for diagnosing pneumonia, a primer for use in the method and a complementary probe to a product amplified by the method. In this method, an amplification target for detecting *Mycoplasma pneumoniae* is DnaJ1 gene. As described, in order to diagnose pneumonia caused by *Mycoplasma*, development of a more practical detection method for *Mycoplasma* by which *Mycoplasma* can be more quickly and easily detected with high sensitivity and accuracy, has been desired.

PRIOR ART DOCUMENTS

Patent Documents

Patent Document 1: Japanese unexamined Patent Application Publication No. 2004-305207.
Patent Document 2: Japanese unexamined Patent Application Publication No. 2012-60925.

Patent Document 3: Japanese unexamined Patent Application Publication No. 2013-515458.

Patent Document 4: International Publication No. WO2011/122034.

Non-Patent Documents

Non-Patent Document 1: International Journal of Medical Microbiology (2009) 299, 291-300.

Non-Patent Document 2: Res. Microbiol. (1993) 144, 489-493.

SUMMARY OF THE INVENTION

Object to be Solved by the Invention

An object of the present invention is to provide a *Mycoplasma* detection method by which a greater number of *Mycoplasma* species can be more quickly and easily detected with high sensitivity and accuracy and a set and kit of a forward primer, a reverse primer and a probe.

Means to Solve the Object

The present inventors conducted intensive studies with a view to attaining the above object. During the studies, they designed a plurality of combinations of a forward primer and reverse primer, which correspond to specific sequences in 16S rRNA gene and 23S rRNA gene having a *Mycoplasma*-specific sequence and the spacer region between both genes, and a probe for detecting a product amplified by use of the primer pair. When they carried out a multiplex real time quantitative PCR using the combinations, they found that a great number of *Mycoplasma* species can be more quickly and easily detected with high sensitivity and accuracy. Based on the finding, they arrived at accomplishment of the present invention.

More specifically, the present invention relates to, (1) A set of a forward primer, a reverse primer and a probe for detecting *Mycoplasma* in a test sample by a multiplex real time quantitative PCR, wherein the set contains one or more forward primers, two or more reverse primers and one or more probes;

the probe(s) is a probe for specifically detecting products amplified by use of the forward primer and the reverse primer;

the forward primer(s) is an oligonucleotide consisting of a nucleotide sequence, which is selected from the group consisting of nucleotide sequences each consisting of continuous 17 to 30 nucleotides in the nucleotide sequence represented by SEQ ID No: 1, and which contains a nucleotide sequence (caaggtatccc) at nucleotide positions 14 to 24 in SEQ ID No: 1; the reverse primers each are an oligonucleotide consisting of a nucleotide sequence, which is selected from the group consisting of nucleotide sequences each consisting of continuous 17 to nucleotides in the one or more nucleotide sequences represented by SEQ ID Nos: 14 and 17 to 20; and the probe(s) is an oligonucleotide, which consists of a nucleotide sequence selected from the group consisting of nucleotide sequences each consisting of continuous 17 to 26 nucleotides in the nucleotide sequence represented by SEQ ID No: 33, or which consists of a complementary nucleotide sequence thereto, (2) the set according to (1), wherein the one or more forward primers are one or more oligonucleotides each consisting of a nucleotide sequence, which is selected from the group consisting of nucleotide sequences each consisting of continuous 17 to 30 nucleotides in the nucleotide sequence represented by SEQ ID No: 1 and which contains a nucleotide sequence (caaggtatccctac) at nucleotide positions 14 to 27 in SEQ ID No: 1, (3) the set according to (1) or (2), wherein the one or more forward primers are one or more oligonucleotides selected from the group consisting of the following (A) and (B):

(A) a forward primer, which is an oligonucleotide consisting of a nucleotide sequence, which is selected from the group consisting of nucleotide sequences each consisting of continuous 17 to 30 nucleotides in the nucleotide sequence represented by SEQ ID No: 2, and which contains a nucleotide sequence at nucleotide positions 14 to 24 in SEQ ID No: 2, and (B) a forward primer, which is an oligonucleotide consisting of a nucleotide sequence, which is selected from the group consisting of nucleotide sequences each consisting of continuous 17 to 30 nucleotides in the nucleotide sequence represented by SEQ ID No: 3, and which contains a nucleotide sequence at nucleotide positions 14 to 24 in SEQ ID No: 3, (4) the set according to any one of (1) to (3), containing two forward primers, wherein the two forward primers are an oligonucleotide consisting of any one of nucleotide sequence selected from SEQ ID Nos: 4 to 7, 11 and 12, and an oligonucleotide consisting of the nucleotide sequence represented by SEQ ID No: 13;

(5) the set according to any one of (1) to (4), wherein at least one of the reverse primers is an oligonucleotide containing a nucleotide sequence (wsccaaggcatccaccah) at nucleotide positions 3 to 20 in SEQ ID No: 14, (6) the set according to any one of (1) to (5), wherein the two or more reverse primers are two or more oligonucleotides selected from the following (C1), (C2-1), (C2-2), (C2-3), (D), (E1), (E2), (F) and (G):

(C1) an oligonucleotide consisting of a nucleotide sequence selected from the group consisting of nucleotide sequences each consisting of continuous 17 to 26 nucleotides in the nucleotide sequence represented by SEQ ID No: 15, (C2-1) an oligonucleotide consisting of a nucleotide sequence selected from the group consisting of nucleotide sequences each consisting of continuous 17 to 26 nucleotides in the nucleotide sequence represented by SEQ ID No: 16 where m at nucleotide position 20 is a, and w at nucleotide position 22 is a, (C2-2) an oligonucleotide consisting of a nucleotide sequence selected from the group consisting of nucleotide sequences each consisting of continuous 17 to 26 nucleotides in the nucleotide sequence represented by SEQ ID No: 16 where m at nucleotide position 20 is c, and w at nucleotide position 22 is a, (C2-3) an oligonucleotide consisting of a nucleotide sequence selected from the group consisting of nucleotide sequences each consisting of continuous 17 to 26 nucleotides in the nucleotide sequence represented by SEQ ID No: 16 where m at nucleotide position 20 is a, and w at nucleotide position 22 is t, (D) an oligonucleotide consisting of a nucleotide sequence selected from the group consisting of nucleotide sequences each consisting of continuous 17 to 26 nucleotides in the nucleotide sequence represented by SEQ ID No: 17, (E1) an oligonucleotide consisting of a nucleotide sequence selected from the group consisting of nucleotide sequences each consisting of continuous 17 to 24 nucleotides in the nucleotide sequence represented by SEQ ID No:

18 where s at nucleotide position 2 is g, and r at each of nucleotide positions 4 and 9 is g, (E2) an oligonucleotide consisting of a nucleotide sequence selected from the group consisting of nucleotide sequences each consisting of continuous 17 to 24 nucleotides in the nucleotide sequence represented by SEQ ID No: 18 where s at nucleotide position 2 is c, and r at each of positions 4 and 9 is a, (F) an oligonucleotide consisting of a nucleotide sequence selected from the group consisting of nucleotide sequences each consisting of continuous 17 to 25 nucleotides in the nucleotide sequence represented by SEQ ID No: 19, and (G) an oligonucleotide consisting of a nucleotide sequence selected from the group consisting of nucleotide sequences each consisting of continuous 17 to 23 nucleotides in the nucleotide sequence represented by SEQ ID No: 20, (7) the set according to any one of (1) to (6), wherein the two or more reverse primers are two or more oligonucleotides selected from the following oligonucleotides:

an oligonucleotide consisting of the nucleotide sequence represented by SEQ ID No: 21, an oligonucleotide consisting of the nucleotide sequence represented by SEQ ID No: 22, an oligonucleotide consisting of the nucleotide sequence represented by SEQ ID No: 24, an oligonucleotide consisting of the nucleotide sequence represented by SEQ ID No: 25, an oligonucleotide consisting of the nucleotide sequence represented by SEQ ID No: 26, an oligonucleotide consisting of the nucleotide sequence represented by SEQ ID No: 27 an oligonucleotide consisting of the nucleotide sequence represented by SEQ ID No: 17, an oligonucleotide consisting of the nucleotide sequence represented by SEQ ID No: 28, an oligonucleotide consisting of the nucleotide sequence represented by SEQ ID No: 29, an oligonucleotide consisting of the nucleotide sequence represented by SEQ ID No: 19, and an oligonucleotide consisting of the nucleotide sequence represented by SEQ ID No: 20, (8) the set according to any one of (1) to (7), wherein the probe is an oligonucleotide containing a nucleotide sequence (sggrtggaty) at nucleotide positions 7 to 16 in SEQ ID No: 33 or a complementary nucleotide sequence thereto, (9) the set according to any one of (1) to (8), wherein the one or more probes are one or more oligonucleotides selected from the following (H) to (L):

(H) an oligonucleotide, which consists of a nucleotide sequence selected from the group consisting of nucleotide sequences each consisting of continuous 17 to 26 nucleotides in the nucleotide sequence represented by SEQ ID No: 34, or which consists of a complementary nucleotide sequence thereto, (I) an oligonucleotide, which consists of a nucleotide sequence selected from the group consisting of nucleotide sequences each consisting of continuous 17 to 26 nucleotides in the nucleotide sequence represented by SEQ ID No: 35 or which consists of a complementary nucleotide sequence thereto, (J) an oligonucleotide, which consists of a nucleotide sequence selected from the group consisting of nucleotide sequences each consisting of continuous 17 to 26 nucleotides in the nucleotide sequence represented by SEQ ID No: 36, or which consists of a complementary nucleotide sequence thereto, (K) an oligonucleotide, which consists of a nucleotide sequence selected from the group consisting of nucleotide sequences each consisting of continuous 17 to 26 nucleotides in the nucleotide sequence represented by SEQ ID No: 37, or which consists of a complementary nucleotide sequence thereto, and (L) an oligonucleotide, which consists of a nucleotide sequence selected from the group consisting of nucleotide sequences each consisting of continuous 17 to 26 nucleotides in the nucleotide sequence represented by SEQ ID No: 38, or which consists of a complementary nucleotide sequence thereto,

(10) the set according to any one of (1) to (9), wherein the one or more probes are one or more oligonucleotides selected from the following (h) to (l):

(h) an oligonucleotide consisting of the nucleotide sequence represented by SEQ ID No: 39, (i) an oligonucleotide consisting of the nucleotide sequence represented by SEQ ID No: 40, (j) an oligonucleotide consisting of the nucleotide sequence represented by SEQ ID No: 41, (k) an oligonucleotide consisting of the nucleotide sequence represented by SEQ ID No: 42, and (l) an oligonucleotide consisting of the nucleotide sequence represented by SEQ ID No: 43, and

(11) the set according to any one of (1) to (10), wherein the probe is TaqMan (registered trade mark) probe having the 5' end modified with a fluorescent substance and the 3' end modified with a quencher.

The present invention also relates to

(12) A kit for detecting *Mycoplasma* in a test sample by a multiplex real time quantitative PCR, wherein the kit has the set of a forward primer, a reverse primer and a probe according to any one of (1) to (11) and a solid support, and the probe is immobilized onto the solid support.

The present invention further relates to

(13) a method for detecting *Mycoplasma* in a test sample by a multiplex real time quantitative PCR, comprising (a) Step a of extracting DNA from the test sample, (b) Step b of performing a multiplex real time quantitative PCR using the DNA extracted in Step a as a template and the forward primer and reverse primer contained in the set according to any one of (1) to (11) or the kit according to (12), and (c) Step c of detecting the presence of *Mycoplasma* in the test sample by detecting a product amplified by the multiplex real time quantitative PCR in Step b by use of the probe contained in the set according to any one of (1) to (11) or in the kit according to (12),

(14) the method for detecting *Mycoplasma* according to (13), wherein the product amplified by the multiplex real time quantitative PCR in Step c is detected by detecting whether or not a specific hybridization with the probe contained in the set according to any one of (1) to (11) or in the kit according to (12) occurs, and

(15) the method for detecting *Mycoplasma* according to (13) or (14), wherein the detection limit (sensitivity) of one or more *Mycoplasma* species selected from the group consisting of *Mycoplasma arginini, Mycoplasma buccale, Mycoplasma faucium, Mycoplasma hominis, Mycoplasma orale, Mycoplasma salivarium, Mycoplasma fermentans, Mycoplasma lipophilum, Mycoplasma primatum, Mycoplasma hyorhinis, Mycoplasma synoviae, Mycoplasma genitalium, Mycoplasma pneumoniae, Acholeplasma laidlawii,*

*Ureaplasma urealyticum, Mycoplasma gallisepticum* and *Spiroplasma citri*, is 10 cfu/mL or less.

Effect of the Invention

According to the present invention, it is possible to provide a detection method for *Mycoplasma* by which a greater number of *Mycoplasma* species can be more quickly and easily detected with high sensitivity and accuracy and a set and kit of a forward primer, a reverse primer and a probe for the detection.

BRIEF DESCRIPTION OF DRAWINGS

FIG. 1 The upper panel shows the positions of the genome of *Mycoplasma* to which individual forward primers and reverse primers correspond. The lower panel shows *Mycoplasma* species targeted by individual sets (combinations) of a forward primer, a probe and a reverse primer.

FIG. 2 shows the results of detection sensitivity to individual *Mycoplasma* species measured by the detection method of the invention (detection method of the present invention) and the detection method described in a reference paper (the detection method of Non-Patent Document 1).

FIG. 3 shows bacteria, fungi and mammal derived cells which did not actually show cross reactivity in the multiplex real time quantitative PCR method of the present invention.

FIG. 4 shows the positional relationship of F1 forward primer and variation primers thereof; and R1 reverse primer and variation primers thereof on the sequence.

FIG. 5 shows the results of the multiplex real time quantitative PCR of the present invention using combinations of F1 forward primer, variation primers thereof, R1 reverse primer and variation primers thereof. The ct value indicates the number of cycles repeated until a PCR amplified product reached a predetermined amount. A smaller ct value shows that a target is detected with a higher sensitivity.

FIG. 6 shows a part of the comparison results between the genomic sequences of *Mycoplasma* (*Mycoplasma arginini, Mycoplasma hyorhinis, Mycoplasma genitalium, Mycoplasma fermentans, Spiroplasma citri*) and the genomic sequence of *Clostridium sporogenes* (a species not belonging to *Mycoplasma*).

FIG. 7-1 shows the results of comparing the genomic sequences in the vicinity of the forward primer, probe and reverse primer of the present invention in *Mycoplasma microti, Mycoplasma penetrans, Mycoplasma iowae, Mycoplasma muris, Ureaplasma urealyticum, Mycoplasma pneumoniae, Mycoplasma genitalium* and *Mycoplasma gallisepticum*.

FIG. 7-2 shows the results of comparing the genomic sequences in the vicinity of the forward primer, probe and reverse primer of the present invention in *Mycoplasma microti, Mycoplasma penetrans, Mycoplasma iowae, Mycoplasma muris, Ureaplasma urealyticum, Mycoplasma pneumoniae, Mycoplasma genitalium* and *Mycoplasma gallisepticum*.

FIG. 7-3 shows the results of comparing the genomic sequences in the vicinity of the forward primer, probe and reverse primer of the present invention in *Mycoplasma microti, Mycoplasma penetrans, Mycoplasma iowae, Mycoplasma muris, Ureaplasma urealyticum, Mycoplasma pneumoniae, Mycoplasma genitalium* and *Mycoplasma gallisepticum*.

MODE OF CARRYING OUT THE INVENTION (Set of Forward Primer, Reverse Primer and Probe of the Present Invention)

A set of a forward primer, a reverse primer and a probe of the present invention (hereinafter also referred to simply as "the set of the present invention") is a set of a forward primer, a reverse primer and a probe for detecting *Mycoplasma* in a test sample by a multiplex real time quantitative PCR. The set contains one or more forward primers, two or more reverse primers and one or more probes. The probe(s) is a probe for specifically detecting a product amplified by use of the forward primer and the reverse primer. The forward primer(s) is an oligonucleotide consisting of a nucleotide sequence, which is selected from the group consisting of nucleotide sequences each consisting of continuous 17 to 30 nucleotides in the nucleotide sequence represented by SEQ ID No: 1, and which contains a nucleotide sequence at nucleotide positions 14 to 24 in the nucleotide sequence represented by SEQ ID No: 1. The reverse primers each are an oligonucleotide consisting of a nucleotide sequence, which is selected from the group consisting of nucleotide sequences each consisting of continuous 17 to 26 nucleotides in the one or more nucleotide sequences represented by SEQ ID Nos: 14 and 17 to 20. The probe(s) is an oligonucleotide, which consists of a nucleotide sequence selected from the group consisting of nucleotide sequences each consisting of continuous 17 to 26 nucleotides in the nucleotide sequence represented by SEQ ID No: 33, or which consists of a complementary nucleotide sequence thereto. The forward primer, reverse primer and probe of the present invention each are not particularly limited as long as they satisfy the aforementioned limitations.

The forward primer of the present invention is not particularly limited as long as it is an oligonucleotide consisting of a nucleotide sequence, which is selected from the group consisting of nucleotide sequences each consisting of continuous 17 to 30 nucleotides (preferably 17 to 26 nucleotides, more preferably 17 to 23 nucleotides, further preferably 18 to 22 nucleotides, still further preferably 19 to 21 nucleotides) in the nucleotide sequence represented by SEQ ID No: 1 and which contains a nucleotide sequence at nucleotide positions 14 to 24 in SEQ ID No: 1. Of these oligonucleotide, in order to detect *Mycoplasma* with a higher sensitivity or accuracy, an oligonucleotide containing a nucleotide sequence at nucleotide positions 11 to 24 in SEQ ID No: 1 and an oligonucleotide containing a nucleotide sequence at nucleotide positions 14 to 27 in SEQ ID No: 1 are preferable; and an oligonucleotide containing a nucleotide sequence at nucleotide positions 11 to 27 in SEQ ID No: 1 is more preferable. The nucleotide c at nucleotide position 27 in SEQ ID No: 1 is extremely highly conserved in *Mycoplasma* species; however, the nucleotide is often not c in other bacteria except *Mycoplasma*. Thus, the nucleotide c at nucleotide position 27 in SEQ ID No: 1 is the characteristic nucleotide specifically observed in *Mycoplasma*.

The set of the present invention may contain a single forward primer, alone. However, in order to detect a greater number of *Mycoplasma* species, at least two forward primers including the following two types: (A) and (B), are preferably contained and the following two types: (A) and (B), are more preferably contained.

(A) a forward primer, which is an oligonucleotide consisting of a nucleotide sequence, which is selected from the group consisting of nucleotide sequences each consisting of continuous 17 to 30 nucleotides (preferably 17 to 26 nucleotides, more preferably 17 to 23 nucleotides, further preferably 18 to 22 nucleotides, still further preferably 19 to 21 nucleotides) in the nucleotide sequence represented by SEQ ID No: 2 (the nucleotide sequence represented by SEQ ID No: 1 in which the nucleotide s at nucleotide position 24 is c), and which contains a nucleotide sequence at nucleotide positions 14 to 24 in SEQ ID No: 2 (superordinate concept of F1 series forward primer); and (B) a forward primer, which is an oligonucleotide consisting of a nucleotide sequence, which is selected from the group consisting of nucleotide sequences each consisting of continuous 17 to 30 nucleotides (preferably 17 to 26 nucleotides, more preferably 17 to 23 nucleotides, further preferably 18 to 22 nucleotides, still further preferably 19 to 21 nucleotides) in the nucleotide sequence represented by SEQ ID No: 3 (the nucleotide sequence represented by SEQ ID No: 1 in which the nucleotide s at nucleotide position 24 is g), and which contains a nucleotide sequence at nucleotide positions 14 to 24 in SEQ ID No: 3 (superordinate concept of F2 forward primer).

As more specific examples of the one or more forward primers contained in the set of the present invention, one or more forward primers, which are oligonucleotides selected from the following (A1) to (A6) and (B1) are preferable. Of them, one or more forward primers, which are oligonucleotides selected from the following (A1) to (A6) and the forward primer, which is an oligonucleotide of the following (B1), are preferably contained.

(A1) An oligonucleotide consisting of a nucleotide sequence selected from the group consisting of nucleotide sequences each consisting of continuous 17 to 21 nucleotides (preferably 18 to 20 nucleotides, more preferably 19 nucleotides) in the nucleotide sequence at nucleotide positions 8 to 30 in SEQ ID No: 2 (a sequence having two nucleotides added to the 5' end of F1 forward primer and two nucleotides added to the 3' end thereof) (superordinate concept of F1 forward primer), (A2) an oligonucleotide consisting of a nucleotide sequence selected from the group consisting of nucleotide sequences each consisting of continuous 17 to 21 nucleotides (preferably 18 to 20 nucleotides, more preferably 19 nucleotides) in the nucleotide sequence at nucleotide positions 9 to 30 in SEQ ID No: 2 (a sequence having two nucleotides added to the 5' end of M1 forward primer and a single nucleotide added to the 3' end thereof) (superordinate concept of M1 forward primer), (A3) an oligonucleotide consisting of a nucleotide sequence selected from the group consisting of nucleotide sequences each consisting of continuous 17 to 21 nucleotides (preferably 18 to 20 nucleotides, more preferably 19 nucleotides) in the nucleotide sequence at nucleotide positions 6 to 28 in SEQ ID No: 2 (a sequence having two nucleotides added to the 5' end of TF forward primer and two nucleotides added to the 3' end thereof) (superordinate concept of TF forward primer), (A4) an oligonucleotide consisting of a nucleotide sequence selected from the group consisting of nucleotide sequences each consisting of continuous 18 to 22 nucleotides (preferably 19 to 21 nucleotides, more preferably 20 nucleotides) in the nucleotide sequence at nucleotide positions 9 to 30 in SEQ ID No: 2 (a sequence having two nucleotides added to the 5' end of MyTF-1 forward primer) (superordinate concept of MyTF-1 forward primer), (A5) an oligonucleotide consisting of a nucleotide sequence selected from the group consisting of nucleotide sequences each consisting of continuous 17 to 21 nucleotides (preferably 18 to 20 nucleotides, more preferably 19 nucleotides) in the nucleotide sequence at nucleotide positions 4 to 26 in SEQ ID No: 2 (a sequence having two nucleotides added to the 5' end of MyTF-5 forward primer and two nucleotides added to the 3' end thereof) (superordinate concept of MyTF-5 forward primer), (A6) an oligonucleotide consisting of a nucleotide sequence selected from the group consisting of nucleotide sequences each consisting of continuous 19 to 23 nucleotides (preferably 20 to 22 nucleotides, more preferably 21 nucleotides) in the nucleotide sequence at nucleotide positions 5 to 29 in SEQ ID No: 2 (a sequence having two nucleotides added to the 5' end of MyTF-6 forward primer and two nucleotides added to the 3' end thereof) (superordinate concept of MyTF-6 forward primer), and (B1) an oligonucleotide consisting of a nucleotide sequence selected from the group consisting of nucleotide sequences each consisting of continuous 17 to 21 nucleotides (preferably 18 to 20 nucleotides, more preferably 19 nucleotides) in the nucleotide sequence at nucleotide positions 8 to 30 in SEQ ID No: 3 (a sequence having two nucleotides added to the 5' end of F2 forward primer and two nucleotides added to the 3' end thereof) (superordinate concept of F2 forward primer).

As the oligonucleotide (A1), the following oligonucleotide (a1) is preferable. As the oligonucleotide (A2), the following oligonucleotide (a2) is preferable. As the oligonucleotide (A3), the following oligonucleotide (a3) is preferable. As the oligonucleotide (A4), the following oligonucleotide (a4) is preferable. As the oligonucleotide (A5), the following oligonucleotide (a5) is preferable. As the oligonucleotide (A6), the following oligonucleotide (a6) is preferable. As the oligonucleotide (B1), the following oligonucleotide (b1) is preferable.

(a1) An oligonucleotide consisting of the nucleotide sequence represented by SEQ ID No: 4 (the nucleotide sequence at nucleotide positions 10 to 28 in SEQ ID No: 2) (F1 forward primer), (a2) an oligonucleotide consisting of the nucleotide sequence represented by SEQ ID No: 5 (the nucleotide sequence at nucleotide positions 11 to 29 in SEQ ID No: 2) (M1 forward primer), (a3) an oligonucleotide consisting of the nucleotide sequence represented by SEQ ID No: 6 (the nucleotide sequence at nucleotide positions 8 to 26 in SEQ ID No: 2) (TF forward primer), (a4) an oligonucleotide consisting of the nucleotide sequence represented by SEQ ID No: 7 (the nucleotide sequence at nucleotide positions 11 to 30 in SEQ ID No: 2) (MyTF-1 forward primer), (a5) an oligonucleotide consisting of the nucleotide sequence represented by SEQ ID No: 11 (the nucleotide sequence at nucleotide positions 6 to 24 in SEQ ID No: 2) (MyTF-5 forward primer), (a6) an oligonucleotide consisting of the nucleotide sequence represented by SEQ ID No: 12 (the nucleotide sequence at nucleotide positions 7 to 27 in SEQ ID No: 2) (MyTF-6 forward primer), and (b1) an oligonucleotide consisting of the nucleotide sequence represented by SEQ ID No: 13 (the nucleotide sequence at nucleotide positions 10 to 28 in SEQ ID No: 3) (F2 forward primer).

Of the aforementioned primers: F1 forward primer, M1 forward primer, TF forward primer, MyTF-1 forward primer, MyTF-5 forward primer and MyTF-6 forward primer (collectively referred to also as "F1 series forward primer"), F1 forward primer, M1 forward primer, TF forward primer, MyTF-1 forward primer and MyTF-5 forward primer are preferable, and in particular, F1 forward primer, MyTF-1 forward primer and MyTF-5 forward primer are more preferable.

The forward primers (A), (A1) to (A6) and (a1) to (a6) are suitable for detecting, for example, *Mycoplasma arginini*, *Mycoplasma buccale*, *Mycoplasma faucium*, *Mycoplasma hominis*, *Mycoplasma orale*, *Mycoplasma salivarium*, *Mycoplasma fermentans*, *Mycoplasma lipophilum*, *Mycoplasma primatum*, *Mycoplasma hyorhinis*, *Mycoplasma synoviae*, *Mycoplasma genitalium*, *Mycoplasma pneumoniae*, *Acholeplasma laidlawii*, *Ureaplasma urealyticum* and *Mycoplasma gallisepticum*. The forward primers (B), (B1) and (b1) are suitable for detecting for example, *Spiroplasma citri*.

The reverse primer of the present invention is not particularly limited as long as it is an oligonucleotide consisting of a nucleotide sequence, which is selected from the group consisting of nucleotide sequences each consisting of continuous 17 to 26 nucleotides (preferably to 25 nucleotides) in the one or more nucleotide sequences represented by SEQ ID Nos: 14 and 17 to 20. The set of the present invention may contain a single reverse primer alone. However, in order to detect a greater number of *Mycoplasma* species, the set preferably contains two or more (preferably three or more, more preferably four or more, further preferably five or more, more preferably six or more, further preferably seven or more, more preferably eight or more, further preferably nine) reverse primers selected from the group consisting of preferably the following (C) to (G) [more preferably (C1), (C2-1), (C2-2), (C2-3), (D), (E1), (E2), (F), (G)].

(C) An oligonucleotide consisting of a nucleotide sequence selected from the group consisting of nucleotide sequences each consisting of continuous 17 to 26 nucleotides (preferably 18 to 24 nucleotides) in the nucleotide sequence represented by SEQ ID No: 14 (superordinate concepts of R1 series and R4 series reverse primers), (D) an oligonucleotide consisting of a nucleotide sequence selected from the group consisting of nucleotide sequences each consisting of continuous 17 to 26 nucleotides (preferably 18 to 26 nucleotides, more preferably 20 to 26 nucleotides) in the nucleotide sequence represented by SEQ ID No: 17 (superordinate concept of R2 reverse primer), (E) an oligonucleotide consisting of a nucleotide sequence selected from the group consisting of nucleotide sequences each consisting of continuous 17 to 24 nucleotides (preferably 18 to 22 nucleotides) in the nucleotide sequence represented by SEQ ID No: 18 (superordinate concepts of R3 and R6 reverse primers), (F) an oligonucleotide consisting of a nucleotide sequence selected from the group consisting of nucleotide sequences each consisting of continuous 17 to 25 nucleotides (preferably 18 to 25 nucleotides, more preferably 20 to 25 nucleotides) in the nucleotide sequence represented by SEQ ID No: 19 (superordinate concept of R5 reverse primer), and (G) an oligonucleotide consisting of a nucleotide sequence selected from the group consisting of nucleotide sequences each consisting of continuous 17 to 23 nucleotides (preferably 18 to 23 nucleotides, more preferably 20 to 23 nucleotides) in the nucleotide sequence represented by SEQ ID No: 20 (superordinate concept of R7 reverse primer).

As the oligonucleotide (C), the following oligonucleotides (C1) and (C2) are preferable.

(C1) An oligonucleotide consisting of a nucleotide sequence selected from the group consisting of nucleotide sequences each consisting of continuous 17 to 26 nucleotides (preferably 18 to 24 nucleotides) in the nucleotide sequence represented by SEQ ID No: 15 (superordinate concept of R1 series reverse primer), and (C2) an oligonucleotide consisting of a nucleotide sequence selected from the group consisting of nucleotide sequences each consisting of continuous 17 to 26 nucleotides (preferably 20 to 26 nucleotides) in the nucleotide sequence represented by SEQ ID No: 16 (superordinate concept of R4 series reverse primer).

As the oligonucleotide (C1), the following oligonucleotides (c1-1), (c1-2) and (c1-3) are preferable. Of them, oligonucleotide (c1-1) is more preferable.

(c1-1) An oligonucleotide consisting of the nucleotide sequence represented by SEQ ID No: 21 (nucleotide sequence at nucleotide positions 1 to 23 in SEQ ID No: 15) (R1 reverse primer), (c1-2) an oligonucleotide consisting of the nucleotide sequence represented by SEQ ID No: 22 (nucleotide sequence at nucleotide positions 1 to 22 in SEQ ID No: 15) (M6-2 reverse primer), and (c1-3) an oligonucleotide consisting of the nucleotide sequence represented by SEQ ID No: 24 (nucleotide sequence at nucleotide positions 3 to 20 in SEQ ID No: 15) (TR-2 reverse primer).

As the oligonucleotide (C2), the following oligonucleotides (C2-1), (C2-2) and (C2-3) are preferable.

(C2-1) An oligonucleotide consisting of a nucleotide sequence selected from the group consisting of nucleotide sequences each consisting of continuous 17 to 26 nucleotides (preferably 18 to 24 nucleotides) in the nucleotide sequence represented by SEQ ID No: 16 where m at nucleotide position 20 is a and w at nucleotide position 22 is a (in the nucleotide sequence represented by SEQ ID No: 16, the nucleotide sequence (mawa) at nucleotide positions 20 to 23 is the nucleotide sequence (aaaa) represented by SEQ ID No: 30) (superordinate concept of R4-1 reverse primer), (C2-2) an oligonucleotide consisting of a nucleotide sequence selected from the group consisting of nucleotide sequences each consisting of continuous 17 to 26 nucleotides (preferably 18 to 24 nucleotides) in the nucleotide sequence represented by SEQ ID No: 16 where m at nucleotide position 20 is c and w at nucleotide position 22 is a (in the nucleotide sequence represented by SEQ ID No: 16, the nucleotide sequence (mawa) at nucleotide positions 20 to 23 is the nucleotide sequence (caaa) represented by SEQ ID No: 31) (superordinate concept of R4-2 reverse primer), and (C2-3) an oligonucleotide consisting of a nucleotide sequence selected from the group consisting of nucleotide sequences each consisting of continuous 17 to 26 nucleotides (preferably 18 to 24 nucleotides) in the nucleotide sequence represented by SEQ ID No: 16 where m at nucleotide position 20 is a and w at nucleotide position 22 is t (in the nucleotide sequence represented by SEQ ID No: 16, the nucleotide sequence (mawa) at nucleotide positions 20 to 23 is the nucleotide sequence (aata) represented by SEQ ID No: 32) (superordinate concept of R4-3 reverse primer).

As the oligonucleotide (C2-1), the following oligonucleotide (c2-1) is preferable. As the oligonucleotide (C2-2), the following oligonucleotide (c2-2) is preferable. As the oligonucleotide (C2-3), the following oligonucleotide (c2-3) is preferable.

(c2-1) An oligonucleotide consisting of the nucleotide sequence represented by SEQ ID No: 25 (nucleotide sequence at nucleotide positions 3 to 26 of the nucleotide sequence represented by SEQ ID No: 16, where m at nucleotide position 20 is a, and w at nucleotide position 22 is a) (R4-1 reverse primer), (c2-2) an oligonucleotide consisting of the nucleotide sequence represented by SEQ ID No: 26 (nucleotide sequence at nucleotide positions 3 to 26 of the nucleotide sequence represented by SEQ ID No: 16, where m at nucleotide position 20 is c, and w at nucleotide position 22 is a) (R4-2 reverse primer), and (c2-3) an oligonucleotide consisting of the nucleotide sequence represented by SEQ ID No: 27 (nucleotide sequence at nucleotide positions 3 to 26 of the nucleotide sequence represented by SEQ ID No: 16, where m at nucleotide position 20 is a, and w at nucleotide position 22 is t) (R4-3 reverse primer).

As the oligonucleotide (D), the following oligonucleotide (d) is preferable.

(d) An oligonucleotide consisting of the nucleotide sequence represented by SEQ ID No: 17 (R2 reverse primer).

As the oligonucleotide (E), the following oligonucleotides (E1) and (E2) are preferable.

(E1) An oligonucleotide consisting of a nucleotide sequence selected from the group consisting of nucleotide sequences each consisting of continuous 17 to 24 nucleotides (preferably 18 to 22 nucleotides) in the nucleotide sequence represented by SEQ ID No: 18 where s at nucleotide position 2 is g, and r at each of nucleotide positions 4 and 9 is g (superordinate concept of R3 reverse primer), and (E2) an oligonucleotide consisting of a nucleotide sequence selected from the group consisting of nucleotide sequences each consisting of continuous 17 to 24 nucleotides (preferably 18 to 22 nucleotides) in the nucleotide sequence represented by SEQ ID No: 18 where s at nucleotide position 2 is c, and r at each of nucleotide positions 4 and 9 is a (superordinate concept of R6 reverse primer).

As the oligonucleotide (E1), the following oligonucleotide (e1) is preferable. As the oligonucleotide (E2), the following oligonucleotide (e2) is preferable.

(e1) An oligonucleotide consisting of the nucleotide sequence represented by SEQ ID No: 28 (nucleotide sequence at nucleotide positions 5 to 24 in SEQ ID No: 18 where r at nucleotide position 9 is g) (R3 reverse primer), and (e2) an oligonucleotide consisting of the nucleotide sequence represented by SEQ ID No: 29 (nucleotide sequence at nucleotide positions 5 to 24 in SEQ ID No: 18 where r at nucleotide position 9 is a) (R6 reverse primer).

As the oligonucleotide (F), the following oligonucleotide (f) is preferable.

(f) An oligonucleotide consisting of the nucleotide sequence represented by SEQ ID No: 19 (R5 reverse primer).

As the oligonucleotide (G), the following oligonucleotide (g) is preferable.

(g) An oligonucleotide consisting of the nucleotide sequence represented by SEQ ID No: 20 (R7 reverse primer).

The reverse primers (C1), (c1-1), (c1-2) and (c1-3) are suitable for detecting, for example, *Mycoplasma genitalium* and *Mycoplasma pneumoniae*. The reverse primers (C2-1) and (c2-1) are suitable for detecting, for example, *Mycoplasma arginini, Mycoplasma buccale, Mycoplasma faucium, Mycoplasma hominis, Mycoplasma orale* and *Mycoplasma salivarium*. The reverse primers (C2-2) and (c2-2) are suitable for detecting, for example, *Mycoplasma fermentans, Mycoplasma lipophilum* and *Mycoplasma primatum*. The reverse primers (C2-3) and (c2-3) are suitable for detecting, for example, *Mycoplasma hyorhinis*. The reverse primers (D) and (d) are suitable for detecting, for example, *Acholeplasma laidlawii*. The reverse primers (E1) and (e1) are suitable for detecting, for example, *Mycoplasma gallisepticum*. The reverse primers (E2) and (e2) are suitable for detecting, for example, *Ureaplasma urealyticum*. The reverse primers (F) and (f) are suitable for detecting, for example, *Spiroplasma citri*. The reverse primers (G) and (g) are suitable for detecting, for example, *Mycoplasma synoviae*.

The probe of the present invention is not particularly limited as long as it is an oligonucleotide, which consists of a nucleotide sequence selected from the group consisting of nucleotide sequences each consisting of continuous 17 to 26 nucleotides in the nucleotide sequence represented by SEQ ID No: 33, or which consists of a complementary nucleotide sequence thereto. As the probe of the present invention, an oligonucleotide containing a nucleotide sequence (sggrtggaty) at nucleotide positions 7 to 16 in SEQ ID No: 33 or a complementary nucleotide sequence thereto is preferable and an oligonucleotide containing a nucleotide sequence at nucleotide positions 44 to 48 or a complementary nucleotide sequence thereto is more preferable. The set of the present invention may contain a single probe, alone. However, in order to detect a greater number of *Mycoplasma* species, it is preferable that preferably two or more probes, more preferably three or more probes, further preferably four or more probes, and still further preferably five probes selected from the following (H) to (L) are contained.

(H) An oligonucleotide, which consists of a nucleotide sequence selected from the group consisting of nucleotide sequences each consisting of continuous 17 to nucleotides (preferably 19 to 25 nucleotides, more preferably 20 to 24 nucleotides) in the nucleotide sequence represented by SEQ ID No: 34 (the nucleotide sequence represented by SEQ ID No: 33 where s at nucleotide position 33 is g, and r is a, and y is c), or which consists of a complementary sequence thereto (superordinate concept of P1-1 probe), (I) an oligonucleotide, which consists of a nucleotide sequence selected from the group consisting of nucleotide sequences each consisting of continuous 17 to nucleotides (preferably 19 to 25 nucleotides, more preferably 20 to 24 nucleotides) of the nucleotide sequence represented by SEQ ID No: 35 (the nucleotide sequence represented by SEQ ID No: 33 where s at nucleotide position 33 is g, and r is g, and y is t), or which consists of a complementary nucleotide sequence thereto (superordinate concept of P1-2 probe), (J) an oligonucleotide, which consists of a nucleotide sequence selected from the group consisting of nucleotide sequences each consisting of continuous 17 to nucleotides (preferably 19 to 25 nucleotides, more preferably 20 to 24 nucleotides) of the nucleotide sequence represented by SEQ ID No: 36 (the nucleotide sequence represented by SEQ ID No: 33 where s at nucleotide position 33 is g, and r is a, and y is t), or which consists of a complementary nucleotide sequence thereto (superordinate concept of P1-3 probe), (K) an oligonucleotide, which consists of a nucleotide sequence selected from the group consisting of nucleotide sequences each consisting of continuous 17 to nucleotides (preferably 19 to 25 nucleotides, more preferably 20 to 24 nucleotides) of the nucleotide sequence represented by SEQ ID No: 37 (the nucleotide sequence represented by SEQ ID No: 33 where s at nucleotide position 33 is g, and r is g, and y is c), or which consists of a complementary nucleotide sequence thereto (superordinate concept of P1-4 probe), and (L) an oligonucleotide, which consists of a nucleotide sequence selected from the group consisting of nucleotide sequences each consisting of continuous 17 to nucleotides (preferably 19 to 25 nucleotides, more preferably 20 to 24 nucleotides) of the nucleotide sequence represented by SEQ ID No: 38 (the nucleotide sequence represented by SEQ ID No: 33 where s at nucleotide position 33 is c, and r is a, and y is c), or which consists of a complementary nucleotide sequence thereto (superordinate concept of P2 probe)

As the oligonucleotide (H), the following oligonucleotide (h) is preferable. As the oligonucleotide (I), the following oligonucleotide (i) is preferable. As the oligonucleotide (J), the following oligonucleotide (j) is preferable. As the oligonucleotide (K), the following oligonucleotide (k) is preferable. As the oligonucleotide (L), the following oligonucleotide (l) is preferable.

(h) An oligonucleotide consisting of the nucleotide sequence represented by SEQ ID No: 39 (the nucleotide sequence at nucleotide positions 2 to 23 in SEQ ID No: 34) (P1-1 probe), (i) an oligonucleotide consisting of the nucleotide sequence represented by SEQ ID No: 40 (the nucleotide sequence at nucleotide positions 2 to 23 in SEQ ID No: 35) (P1-2 probe), (j) an oligonucleotide consisting of the nucleotide sequence represented by SEQ ID No: 41 (the nucleotide sequence at nucleotide positions 2 to 23 in SEQ ID No: 36) (P1-3 probe), (k) an oligonucleotide consisting of the nucleotide sequence represented by SEQ ID No: 42 (the nucleotide sequence at nucleotide positions 2 to 23 in SEQ ID No: 37) (P1-4 probe), (l) an oligonucleotide consisting of the nucleotide sequence represented by SEQ ID No: 43 (the nucleotide sequence at nucleotide positions 2 to 23 in SEQ ID No: 38) (P2 probe).

The probes (H) and (h) are suitable for detecting, for example, *Mycoplasma arginini*, *Mycoplasma buccale*, *Mycoplasma faucium*, *Mycoplasma hominis*, *Mycoplasma orale*, *Mycoplasma salivarium*, *Mycoplasma fermentans*, *Mycoplasma lipophilum*, *Mycoplasma primatum*, *Mycoplasma hyorhinis*, *Acholeplasma laidlawii* and *Ureaplasma urealyticum*, and more suitable for detecting, in particular, *Mycoplasma arginini*, *Mycoplasma buccale*, *Mycoplasma faucium*, *Mycoplasma hominis*, *Mycoplasma Salivarium*, *Mycoplasma fermentans*, *Mycoplasma Lipophilum*, *Mycoplasma hyorhinis*, *Acholeplasma laidlawii* and *Ureaplasma urealyticum*. The probes (I) and (i) are suitable for detecting, for example, *Mycoplasma gallisepticum*. The probes (J) and (j) are suitable for detecting, for example, *Mycoplasma arginini*, *Mycoplasma buccale*, *Mycoplasma faucium*, *Mycoplasma hominis*, *Mycoplasma orale*, *Mycoplasma salivarium*, *Mycoplasma fermentans*, *Mycoplasma lipophilum*, *Mycoplasma primatum* and *Mycoplasma synoviae*, and more suitable for detecting, in particular, *Mycoplasma orale*, *Mycoplasma primatum* and *Mycoplasma synoviae*. The probes (K) and (k) are suitable for detecting, for example, *Mycoplasma genitalium* and *Mycoplasma pneumoniae*.

The probes (L) and (l) are suitable for detecting, for example, *Spiroplasma citri*.

As a preferable combination of the forward primer, reverse primer and probe of the present invention, CA to CI shown in the following Table 1 can be mentioned. The set of the present invention preferably contain, in order to detect a greater number of *Mycoplasma* species, two (preferably three or more, more preferably four or more, further preferably five or more, more preferably six or more, further preferably seven or more, more preferably eight or more, and particularly preferably nine) combinations selected from combinations CA to CI.

TABLE 1

| Combination name | Primer and probe contained in combination | | |
|---|---|---|---|
| | Forward primer | Reverse primer | Probe corresponding to primer pair |
| CA | (A) (e.g. F1) | (C2-1) (e.g. R4-1) | (H) (e.g. P1-1) or (J) (e.g. P1-3) |
| CB | (A) (e.g. F1) | (C2-2) (e.g. R4-2) | (H) (e.g. P1-1) or (J) (e.g. P1-3) |
| CC | (A) (e.g. F1) | (C2-3) (e.g. R4-3) | (H) (e.g. P1-1) |
| CD | (A) (e.g. F1) | (G) (e.g. R7) | (J) (e.g. P1-3) |
| CE | (A) (e.g. F1) | (C1) (e.g. R1) | (K) (e.g. P1-4) |
| CF | (A) (e.g. F1) | (D) (e.g. R2) | (H) (e.g. P1-1) |
| CG | (A) (e.g. F1) | (E1) (e.g. R3) | (H) (e.g. P1-1) |
| CH | (A) (e.g. F1) | (E2) (e.g. R6) | (I) (e.g. P1-2) |
| CI | (B) (e.g. F2) | (F) (e.g. R5) | (L) (e.g. P2) |

Examples of detection targets of combination CA include *Mycoplasma arginini*, *Mycoplasma buccale*, *Mycoplasma faucium*, *Mycoplasma hominis*, *Mycoplasma orale* and *Mycoplasma salivarium*. Examples of detection targets of combination CB include *Mycoplasma fermentans*, *Mycoplasma lipophilum* and *Mycoplasma primatum*. Examples of detection targets of combination CC include *Mycoplasma hyorhinis*. Examples of detection targets of combination CD include *Mycoplasma synoviae*. Examples of detection targets of combination CE include *Mycoplasma genitalium* and *Mycoplasma pneumoniae*. Examples of detection targets of combination CF include *Acholeplasma laidlawii*. Examples of detection targets of combination CG include *Mycoplasma gallisepticum*. Examples of detection targets of combination CH include *Ureaplasma urealyticum*. Examples of detection targets of combination CI include *Spiroplasma citri*.

The forward primers and reverse primers mentioned above can be each used as a primer in the present invention, as long as it can be used for amplifying a target nucleic acid specific to *Mycoplasma* species as a detection target, even if it has deletion, substitution or addition of one or several nucleotides (for example, 1 to 5 nucleotides, preferably 1 to 3 nucleotides, more preferably 1 to 2 nucleotides, further preferably a single nucleotide) in the nucleotide sequence. The forward primers and reverse primers of the present invention can be synthesized by a conventional method such as a triethyl phosphate method and a phosphoric diester method using e.g. a DNA synthesizer commonly employed.

The probe of the present invention is a single stranded nucleic acid capable of forming a double stranded molecule (hybrid) by hybridizing specifically to a product (amplicon) amplified by use of the corresponding primer pair. As the single stranded nucleic acid, a single stranded DNA is preferably mentioned since it is excellent in stability as a probe. Each of the probes can be used as the probe of the present invention if it is a nucleotide sequence having a sequence identity of 85% or more (preferably 90% or more, more preferably 95% or more, further preferably 98% or more) with each of the nucleotide sequences and can hybridize specifically with a detection target, i.e., an amplified product of *Mycoplasma* species. The probe of the present invention can be synthesized by a conventional method such as a triethyl phosphate method and a phosphoric diester method using e.g., a DNA synthesizer commonly employed.

The probe of the present invention is preferably labeled with a marker substance for detecting a product amplified by use of the corresponding primer pair, more preferably labeled with a fluorescent substance in order to quickly detect an amplified product with high sensitivity, more preferably double-labeled with a fluorescent substance and a quencher, and is further preferably a TaqMan (registered trade mark) probe. The TaqMan probe is a nucleic acid probe usually having the 5' end modified with a fluorescent substance (reporter fluorescent dye) and the 3' end modified with a quencher (quenching fluorescent dye). Examples of the reporter fluorescent dye include fluorescein-based fluorescent dyes such as 6-FAM (6-carboxyfluorescein), TET (6-carboxy-4,7,2',7'-tetrachlorofluorescein) and HEX (6-carboxy-2',4',7',4,7-hexachlorofluorescein). Examples of the quenching fluorescent dye include rhodamine type fluorescent dyes such as 6-carboxytetramethylrhodamine (TAMRA) and 6-carboxy-X-rhodamine (ROX). In the present invention, the nucleotide sequence represented by SEQ ID No: 5 is used; at the same time, a non-fluorescent quenching material. i.e., a minor groove binder (MGB), is suitably used in order to increase the Tm value of the nucleotide sequence by about 8 to 10° C. than the Tm value of the corresponding primer pair. These fluorescent dyes are known in the art and contained in commercially available real time PCR kits. The fluorescent dyes contained in the kit can be used.

(Kit of the Present Invention)

A kit of the present invention for detecting *Mycoplasma* in a test sample by a multiplex real time quantitative PCR (hereinafter also referred to simply as "the kit of the present invention") is not particularly limited as long as it contains a set of a forward primer, a reverse primer and a probe and a solid support and the probe is immobilized onto the solid support. A probe immobilized onto a solid support is preferably used because an amplified product can be more quickly detected. The "solid support" of the present invention refers to a base material to which the oligonucleotide of the probe can be bound. Examples thereof include a microplate (microtiter plate), membrane (e.g., nylon, nitrocellulose), beads (e.g., resin), fine metal particles and a substrate (e.g., glass, silicon, resin). A probe is immobilized onto a solid support via either covalent bonding or noncovalent bonding. When a microplate is used, a probe solution may be added dropwise in wells and simply dried.

(Method for Detecting *Mycoplasma*)

A method for detecting *Mycoplasma* according to the present invention is not particularly limited as long as it is a method for detecting *Mycoplasma* in a test sample by a multiplex real time quantitative PCR, comprising (a) Step a of extracting DNA from the test sample, (b) Step b of performing a multiplex real time quantitative PCR using the DNA extracted in Step a as a template and the set of the primer pair of the present invention or the kit of the present invention and (c) Step c of detecting the presence of *Mycoplasma* in the test sample by detecting a product amplified by the multiplex real time quantitative PCR in Step b.

Owing to the method, a greater number of *Mycoplasma* species can be more quickly and easily detected with high sensitivity and accuracy.

The "*Mycoplasma*" in the present invention refers to not only bacteria belonging to the genus *Mycoplasma* but also bacteria belonging to the class Mollicutes, which includes the genus *Mycoplasma*, the genus *Ureaplasma*, the genus *Mesoplasma*, the genus *Entomoplasma*, the genus *Spiroplasma*, the genus *Acholeplasma*, the genus *Asteroleplasma* and the genus *Thermoplasma*. Of them, bacteria belonging to the genus *Mycoplasma*, the genus *Ureaplasma*, the genus *Spiroplasma* and the genus *Acholeplasma* are preferably mentioned. Of them, bacteria belonging to the genus *Mycoplasma* are more preferably mentioned. A particularly preferable *Mycoplasma* as a detection target of the present invention is one or more *Mycoplasma* species selected from the group consisting of *Mycoplasma arginini*, *Mycoplasma buccale*, *Mycoplasma faucium*, *Mycoplasma hominis*, *Mycoplasma orale*, *Mycoplasma salivarium*, *Mycoplasma fermentans*, *Mycoplasma lipophilum*, *Mycoplasma primatum*, *Mycoplasma hyorhinis*, *Mycoplasma synoviae*, *Mycoplasma genitalium*, *Mycoplasma pneumoniae*, *Acholeplasma laidlawii*, *Ureaplasma urealyticum*, *Mycoplasma gallisepticum* and *Spiroplasma citri*.

The "test sample" of the present invention is not particularly limited. Examples thereof include cultured cells, cell culture supernatants and biological samples of animals such as mammals, reptiles, amphibians and birds and plants. Note that, before DNA is extracted from a test sample, if necessary, a pretreatment such as filtration and removal of contamination may be carried out.

Step a mentioned above is not particularly limited as long as it is a step of extracting DNA from a test sample. As a method for extracting DNA from a test sample, a conventional method can be used. Examples thereof that can be used include a liquid-liquid extraction method such as a phenol/chloroform method and a solid-liquid extraction method using a carrier. Alternatively, various types of DNA extraction kits commercially available from reagent manufacturers, such as QIAamp (registered trade mark), DNA Mini Kit (manufactured by QIAGEN) and Loopamp (registered trade mark) SR DNA extraction kit (manufactured by Eiken Chemical Co., Ltd.), may be used.

A case where DNA is extracted from a test sample by use of QIAamp (registered trade mark) DNA Mini Kit (manufactured by QIAGEN) will be described below.

A test sample (200 μL) is taken and placed in a microtube. To the sample in the microtube, 20 μL of proteinase K and 200 μL of Buffer AL are added and then the mixture is stirred by a vortex for 15 seconds. The temperature of the microtube is kept at 56° C. for 10 minutes. To the sample, 200 μL of ethanol (100%) is added and then the mixture is stirred by a vortex for 15 seconds. The sample is transferred to a QIAamp Mini spin Column (equipped with a 2 mL-collection tube) and centrifuged at room temperature and at 6000×g for one minute. The sample in the QIAamp Mini spin Column is transferred to a new 2 mL-collection tube and 500 μL of Buffer AW1 is added to the sample. The mixture is centrifuged at room temperature and at 6000×g for one minute. The sample in the QIAamp Mini spin Column is transferred to a new 2 mL-collection tube and 500 μL of Buffer AW2 is added to the sample. The mixture is centrifuged at room temperature and at 20000×g for 3 minutes. The sample in the QIAamp Mini spin Column is transferred to a new 2 mL-collection tube and centrifuged at room temperature at 20000×g for one minute. The sample in the QIAamp Mini spin Column is transferred to a 1.5 mL-tube and 200 μL of Buffer AE is added to a membrane. The sample was kept at room temperature for one minute and centrifuged at room temperature and at 6000×g for one minute to obtain a DNA extract. The column is discarded.

Step b mentioned above is not particularly limited as long as it is a step of performing a multiplex real time quantitative PCR using the DNA extracted in Step a as a template and the set of a primer pair of the present invention or the kit of the present invention. The multiplex real time quantitative PCR is real time quantitative PCR using a plurality of primer pairs (2 pairs or more or 3 pairs or more) simultaneously in a single reaction site for amplification. The real time quantitative PCR (real time PCR) is a method of monitoring and analyzing the amount of product amplified by PCR in real time. The multiplex real time quantitative PCR requires no electrophoresis and is excellent in speed and quantitative performance. Such a multiplex real time quantitative PCR can be performed in accordance with a general operation of the multiplex real time quantitative PCR except that DNA extracted in the Step a is used as a template and the set of a primer pair of the present invention or the kit of the present invention is used. The general operation of the multiplex real time quantitative PCR is described, for example, in "Molecular Cloning, fourth edition" (Green and Sambrook, Cold Spring Harbor Laboratory Press, 2012) and an instruction manual for a multiplex real time quantitative PCR kit (for example, Brilliant Multiplex QPCR Master Mix (manufactured by Agilent Technologies)). As a method of detecting an amplified product by a real time quantitative PCR, an intercalator method and a probe method are commonly known. In order to detect *Mycoplasma* with high sensitivity and accuracy, the probe method, i.e., a method of detecting an amplified product by use of a probe, is preferable.

The concentrations of the forward primer, reverse primer and probe to be used in the present invention, are not particularly limited as long as *Mycoplasma* can be detected. The concentrations of them when used can be appropriately controlled by those skilled in the art. The concentrations that can be used, for example, fall within the range of 0.005 to 3 µM and preferably within the range of 0.01 to 1 µM.

As a preferable multiplex real time quantitative PCR method, for example, the following methods A and B can be mentioned.

(Method A)

In a 0.2 mL-tube, a reaction solution (40 µL) and 10 µL of a DNA solution derived from a test sample are added. The total solution (50 µL) can be subjected to a PCR reaction. The PCR reaction solution can be prepared by blending a 1×PCR Gold Buffer (15 mM Tris-HCl (pH8.0), 50 mM KCl) (manufactured by ABI), 3 mM $MgCl_2$ (manufactured by ABI), 60 mM trehalose, 200 µM each dNTPs (manufactured by Trilink)), 1.25 U of amplitaq Gold DNA polymerase, a forward primer (0.5 µM of F1 primer, 0.2 µM of F2 primer) (production is outsourced to TSUKUBA OLIGO SERVICE CO., LTD.), a reverse primer (0.5 µM of R1 primer, 0.3 µM of R2 primer, 0.15 µM of R3 primer, 0.125 µM of R4-1 primer, 0.125 µM of R4-2 primer, 0.125 µM of R4-3 primer, 0.2 µM of R5 primer, 0.15 µM of R6 primer, 0.125 µM of R7 primer) (production is outsourced to TSUKUBA OLIGO SERVICE CO., LTD.) and a fluorescent probe (0.045 µM of P1-1 probe, 0.045 µM of P1-2 probe, 0.045 µM of P1-3 probe, 0.045 µM of P1-4 probe and 0.002 µM of P2 probe) (production is outsourced to TSUKUBA OLIGO SERVICE CO., LTD.). As the PCR, a cycle consisting of an activation step at 95° C. for 10 minutes, a denaturation step at 95° C. for 15 seconds and an annealing/extension (signal detection) at 60° C. for one minute, can be repeated for 45 times. The concentration of PCR product can be calculated by detecting a signal from the fluorescent probe. The multiplex real time quantitative PCR test can be performed by use of a real time PCR system called LightCycler 480 (manufactured by Roche diagnostics). As a negative control, Distilled Water Deionized, Sterile (manufactured by Nippon Gene Co., Ltd.) can be used.

(Method B)

In a 0.2 mL-tube, a reaction solution (40 µL) and 10 µL of a DNA solution derived from a test sample are added. The total solution (50 µL) can be subjected to a PCR reaction. The PCR reaction solution can be prepared by blending 1×PCR Buffer (75 mM Tris-HCl (pH8.8), 20 mM $(NH_4)_2SO_4$, 3 mM $MgCl_2$, 0.01% (v/v) Tween 20, 250 µM each dNTPs), 1.25 U of Taq DNA polymerase (manufactured by Thermo scientific), 5 µg of anti-taq high (manufactured by TOYOBO), a forward primer (0.5 µM of F1 primer, 0.2 µM of F2 primer) (production is outsourced to TSUKUBA OLIGO SERVICE CO., LTD.), a reverse primer (0.5 µM of R1 primer, 0.3 µM of R2 primer, 0.15 µM of R3 primer, 0.125 µM of R4-1 primer, 0.125 µM of R4-2 primer, 0.125 µM of R4-3 primer, 0.2 µM of R5 primer, 0.15 µM of R6 primer, 0.125 µM of R7 primer) (production is outsourced to TSUKUBA OLIGO SERVICE CO., LTD.) and a fluorescent probe (0.045 µM of P1-1 primer, 0.045 µM of P1-2 primer, 0.045 µM of P1-3 primer, 0.045 µM of P1-4 primer and 0.002 µM of P2 primer) (production is outsourced to TSUKUBA OLIGO SERVICE CO., LTD.). As the PCR, a cycle consisting of a pre-denaturation step at 95° C. for one minute, a denaturation step at 95° C. for 5 seconds and an annealing/extension (signal detection) at 60° C. for one minute can be repeated for 45 times. The concentration of a PCR product can be calculated by detecting a signal from the fluorescent probe. The multiplex real time quantitative PCR test can be performed by use of a real time PCR system called LightCycler 480 (manufactured by Roche diagnostics). As a negative control, Distilled Water Deionized, Sterile (manufactured by Nippon Gene Co., Ltd.) can be used.

The multiplex real time quantitative PCR and detection of an amplified product can be performed by use of a commercially available real time PCR system, such as LightCycler 480 (manufactured by Roche diagnostics).

In the method for detecting *Mycoplasma* of the present invention, the detection limit (sensitivity) of *Mycoplasma* is usually 100 cfu/mL or less, preferably 10 cfu/mL or less and more preferably 5 cfu/mL or less. In particular, the detection limits (sensitivity) of *Mycoplasma arginini* (preferably ATCC 23838), *Mycoplasma fermentans* (preferably NBRC15854), *Mycoplasma gallisepticum* (preferably NBRC14855), *Mycoplasma hyorhinis* (preferably NBRC14858), *Mycoplasma orale* (preferably NBRC14477), *Mycoplasma pneumoniae* (preferably NBRC14401), *Mycoplasma synoviae* (preferably ATCC25204), *Acholeplasma laidlawii* (preferably NBRC14400) and *Spiroplasma citri* are preferably 10 cfu/mL or less and more preferably 5 cfu/mL or less.

Now, the present invention will be more specifically described below by way of Examples; however, the present invention is not limited by these Examples.

EXAMPLE 1

[Design of Primer and Probe for Detecting *Mycoplasma*]

Figure 6:
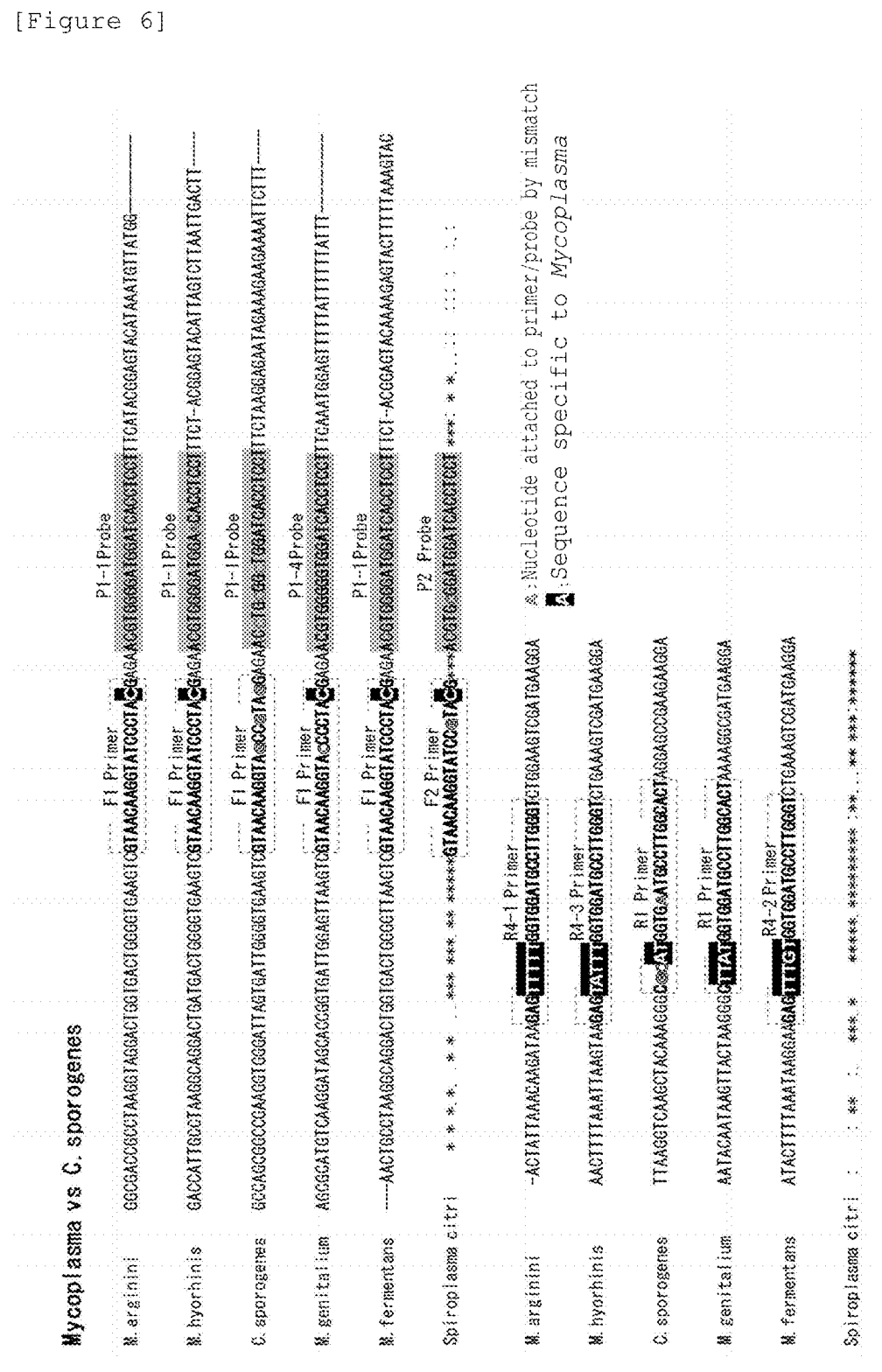

To design primers and probes which can specifically detect an extremely greater number of *Mycoplasma* species, the genomic sequences of *Mycoplasma* species described in FIG. 1, the lower panel (in the column of "Mollicutes species") and the genomic sequences of other bacteria, fungi and mammals described in FIG. 3 were collected, aligned and analyzed. As a result, it was found that a predetermined region out of 16S rRNA gene, 23S rRNA gene and the spacer region between both genes is relatively highly conserved among *Mycoplasma* species even though *Mycoplasma* species have characteristic sequences to individual species. Based on the predetermined region, primers and probes which can specifically detect a great number of *Mycoplasma* species were designed. More specifically, a sequence which anneals with the genomic sequence of the predetermined region of *Mycoplasma* or a complementary sequence thereto and which presumably does not anneal with the genomic sequence or a complementary sequence of the region of other bacteria (mismatch frequently occurs) was employed as the sequence of a forward primer or a reverse primer. A sequence, which hybridizes with the sequence of another predetermined region contained in a product amplified by use of these primers or a complementary sequence thereto and which presumably does not hybridize with the like sequence or a complementary sequence of other bacteria was determined as the sequence of a probe (see, FIG. 1, upper panel and FIG. 7-1 to FIG. 7-3). As an example, the results of comparing the genomic sequences of *Mycoplasma* (*Mycoplasma arginini*, *Mycoplasma hyorhinis*, *Mycoplasma genitalium*, *Mycoplasma fermentans*, *Spiroplasma citri*) to the genomic sequence of *Clostridium sporogenes* (not belonging to *Mycoplasma*) are partly shown in FIG. 6.

As is apparent from the lower panel of FIG. 1, F1 forward primer (SEQ ID No: 4), R4-1 reverse primer (SEQ ID No: 25) and P1-1 (SEQ ID No: 39) or P1-3 (SEQ ID No: 41) probe constitute a set (combination A) targeting *Mycoplasma* of Group 1a; F1 forward primer (SEQ ID No: 4), R4-2 reverse primer (SEQ ID No: 26) and P1-1 (SEQ ID No: 39) or P1-3 (SEQ ID No: 41) probe constitute a set (combination B) of targeting *Mycoplasma* of Group 1b; F1 forward primer (SEQ ID No: 4), R4-3 reverse primer (SEQ ID No: 27) and P1-1 probe (SEQ ID No: 39) constitute s set (combination C) targeting *Mycoplasma* of Group 1c; F1 forward primer (SEQ ID No: 4), R7 reverse primer (SEQ ID No: 20) and P1-3 probe (SEQ ID No: 41) constitute a set (combination D) targeting *Mycoplasma* of Group 6; F1 forward primer (SEQ ID No: 4), R1 reverse primer (SEQ ID No: 21) and P1-4 probe (SEQ ID No: 42) constitute a set (combination E) targeting *Mycoplasma* of Group 2; F1 forward primer (SEQ ID No: 4), R2 reverse primer (SEQ ID No: 17) and P1-1 probe (SEQ ID No: 39) constitute a set (combination F) targeting *Mycoplasma* of Group 4; F1 forward primer (SEQ ID No: 4), R3 reverse primer (SEQ ID No: 28) and P1-1 probe (SEQ ID No: 39) constitute a set (combination G) targeting *Mycoplasma* of Group 3a; F1 forward primer (SEQ ID No: 4), R6 reverse primer (SEQ ID No: 29) and P1-2 probe (SEQ ID No: 40) constitute a set (combination H) targeting *Mycoplasma* of Group 3b; and F2 forward primer (SEQ ID No: 13), R5 reverse primer (SEQ ID No: 19) and P2 probe (SEQ ID No: 43) constitute a set (combination I) targeting *Mycoplasma* of Group 5. Note that, as is apparent from the lower panel of FIG. 1, the detection targets of combination A are *Mycoplasma arginini*, *Mycoplasma buccale*, *Mycoplasma faucium*, *Mycoplasma hominis*, *Mycoplasma orale* and *Mycoplasma salivarium*; the detection targets of combination B are *Mycoplasma fermentans*, *Mycoplasma lipophilum* and *Mycoplasma primatum*; the detection target of combination C is *Mycoplasma hyorhinis*; the detection target of combination D is *Mycoplasma synoviae*; the detection targets of combination E are *Mycoplasma genitalium* and *Mycoplasma pneumoniae*; the detection target of combination F is *Acholeplasma laidlawii*; the detection target of combination G is *Mycoplasma gallisepticum*; the detection target of combination H is *Ureaplasma urealyticum*; and the detection target of combination I is *Spiroplasma citri*. Individual primers and probes of Sets A to I were synthesized by an oligonucleotide synthesizer.

EXAMPLE 2

[Test for Measuring Detection Sensitivity to *Mycoplasma* by Primer-Probe Set]

To check the *Mycoplasma* detection sensitivity of the individual primers and probes of set A to I prepared in Example 1, the following multiplex real time quantitative PCR test was carried out.

(Materials)

*Mycoplasma arginini* (ATCC23838), *Mycoplasma fermentans* (NBRC15854), *Mycoplasma gallisepticum* (NBRC14855), *Mycoplasma hyorhinis* (NBRC14858), *Mycoplasma orale* (NBRC14477), *Mycoplasma pneumoniae* (NBRC14401), *Mycoplasma synoviae* (ATCC25204), *Acholeplasma laidlawii* (NBRC14400) and *Spiroplasma citri* (ATCC27556).

5 Units/μL Amplitaq Gold DNA polymerase (manufactured by ABI).

Reagents provided together with Ampitaq Gold (ABI): 10×PCR Buffer (150 mM Tris-HCl, pH 8.0, 500 mM KCl), 25 mM $MgCl_2$, 10 mM each dNTP mix.

Distilled Water, Deionized, Sterile (manufactured by Nippon Gene Co., Ltd.).

(Method: Method A)

In a 0.2 mL-tube, a reaction solution (40 μL) and 10 μL of a DNA solution (5, 10, 100 or 1000 cfu/reaction) of any one of *Mycoplasma* species mentioned above were added. The total solution (50 μL) was subjected to a PCR reaction. The PCR reaction solution was prepared by blending a 1×PCR Gold Buffer (15 mM Tris-HCl (pH8.0), 50 mM KCl) (manufactured by ABI), 3 mM $MgCl_2$ (manufactured by ABI), 60 mM trehalose, 200 μM each dNTPs (manufactured by ABI)), 1.25 U of amplitaq Gold DNA polymerase, a forward primer (0.5 μM of F1 primer, 0.2 μM of F2 primer) (production was outsourced to TSUKUBA OLIGO SERVICE CO., LTD.), a reverse primer (0.5 μM of R1 primer, 0.3 μM of R2 primer, 0.15 μM of R3 primer, 0.125 μM of R4-1 primer, 0.125 μM of R4-2 primer, 0.125 μM of R4-3 primer, 0.2 μM of R5 primer, 0.15 μM of R6 primer, 0.125 μM of R7 primer) (production was outsourced to TSUKUBA OLIGO SERVICE CO., LTD.) and a fluorescent probe (0.045 μM of P1-1 probe, 0.045 μM of P1-2 probe, 0.045 μM of P1-3 probe, 0.045 μM of P1-4 probe and 0.002 μM of P2 probe) (production was outsourced to TSUKUBA OLIGO SERVICE CO., LTD.). As the PCR, a cycle consisting of an activation step at 95° C. for 10 minutes, a denaturation step at 95° C. for 15 seconds, an annealing/extension (signal detection) at 60° C. for one minute, was repeated for 45 times. The concentration of a PCR product was calculated by detecting a signal from the fluorescent probe. The multiplex real time quantitative PCR test was performed by use of a real time PCR system called Light-Cycler 480 (manufactured by Roche diagnostics).

The results of this test are shown in FIG. 2, left column ("Detection method of invention"). As a comparative method, the conserved region of tuf gene was subjected to a conventional multiplex real time quantitative PCR method (Non-Patent Document 1). The results are shown in FIG. 2, right column ("Detection method of reference paper"). From these results, it was shown that in the detection method of the present invention, the same or more excellent detection sensitivity is obtained compared to that of the conventional analogous detection method. To be more specific, *Mycoplasma fermentans* (5 cfu/reaction) all in 3 samples was not detected (0/3) by the comparative method; however *Mycoplasma fermentans* (5 cfu/reaction) all in 3 samples was detected (3/3) by the detection method of the present invention. It was shown that sensitivity of the detection method of the present invention for detecting *Mycoplasma gallisepticum, Mycoplasma orale, Mycoplasma synoviae, Acholeplasma laidlawii* and *Spiroplasma citri* is extremely excellent compared to the comparative method.

EXAMPLE 3

[Verification of Cross Reactivity with Bacteria Except *Mycoplasma*]

Whether each of forward primers, reverse primers and probes used in the multiplex real time quantitative PCR method of the present invention has cross reactivity with other bacteria except *Mycoplasma*, fungi and mammal derived cells was checked. As the other bacteria etc., the microbes etc. shown in FIG. 3 were subjected to the multiplex real time quantitative PCR method of the present invention, which was carried out in the same manner as in Example 2. As a result, signals from fluorescent probes were not detected. From this, it was found that the primers and probes do not have cross reactivity with bacteria, fungi and mammal derived cells shown in FIG. 3. Other than these, gene sequence information of *Bacillus anthracis, Bacillus cereus, Bacillus thuringiensis, Bartonella bacilliformis, Bartonella grahamii, Borrelia duttonii, Borrelia recurrentis, Campylobacter curvus, Campylobacter hominis, Chlamydia muridarum, Chlamydia trachomatis, Chlamydophila pneumonia, Clostridium botulinum, Clostridium perfringens, Clostridium tetani, Corynebacterium diphtheriae, Erysipelothrix rhusiopathiae, Fusobacterium necrophorum, Haemophilus influenza, Helicobacter pylori, Kineococcus radiotolerans, Lactobacillus brevis, Lactobacillus helveticus, Listeria monocytogenes, Listeria welshimeri* serovar6b str, *Micrococcus luteus, Moraxella catarrhalis, Moraxella lacunata, Mycobacterium gilvum, Mycobacterium tuberculosis, Neisseria gonorrhoeae, Neisseria meningitidis* alpha 14, *Nocardia carnea, Nocardia farcinica, Pediococcus pentosaceus, Pseudomonas putida, Rhodococcus jostii, Rickettsia africae, Rickettsia peacockii, Streptococcus sanguinis, Streptococcus suis, Streptococcus thermophilus, Treponema denticola, Treponema pallidum* were obtained from known sequence database and compared to the sequences of forward primers, reverse primers and probes of the present invention. As a result, it was presumed that the cross reactivity with *Mycoplasma* in the multiplex real time quantitative PCR method of the present invention is denied. It was shown or presumed that the multiplex real time quantitative PCR method of the present invention has no cross reactivity with a great number of bacteria etc. except *Mycoplasma*, as shown in FIG. 3, and is extremely high in specificity to *Mycoplasma*.

EXAMPLE 4

[Verification of Sensitivity and Cross Reactivity of Variation Primers]

F1 forward primer, R1 reverse primer, or primers prepared by modifying them (referred to as "variation primers") were checked for sensitivity for detecting *Mycoplasma* and cross reactivity with *Lactobacillus bulgaricus*.

The forward primers shown in the following Table 2 were designed as variations of F1 forward primer and synthesized by an oligonucleotide synthesizer. Note that, the number of nucleotides of these variation primers and the relationship with F1 forward primer (the types and number of nucleotides added or deleted from the 5' end or 3' end of F1 forward primer) are shown in the following Table.

TABLE 2

| Name of variation forward primer | SEQ ID No. | Number of nucleotides | Relationship with F1 forward primer |
|---|---|---|---|
| M1 | 5 | 19 | 1 nucleotide is deleted from 5' end<br>1 nucleotide is added to 3' end |
| TF | 6 | 19 | 2 nucleotides are added to 5' end<br>2 nucleotides aredeleted from 3' end |
| MyTF-1 | 7 | 20 | 1 nucleotide is deleted from 5' end<br>2 nucleotides are added to 3' end |
| MyTF-2 | 8 | 21 | 10 nucleotides are added to 5' end<br>8 nucleotides are deleted from 3' end |
| MyTF-3 | 9 | 22 | 8 nucleotides are added to 5' end<br>5 nucleotides are deleted from 3' end |
| MyTF-4 | 10 | 22 | 10 nucleotides are added to 5' end<br>7 nucleotides are deleted from 3' end |
| MyTF-5 | 11 | 19 | 4 nucleotides are added to 5' end<br>4 nucleotides are deleted from 3' end |
| MyTF-6 | 12 | 21 | 3 nucleotides are added to 5' end<br>1 nucleotide is deleted from 3' end |

The reverse primers shown in Table 3 were designed as variations of R1 reverse primer and synthesized by an oligonucleotide synthesizer. Note that, the number of nucleotides of these modified primers and the relationship with R1 reverse primer (the types and number of nucleotides added or deleted from the 5' end or 3' end of R1 reverse primer) are shown in the following Table 3.

TABLE 3

| Name of variation reverse primer | SEQ ID No. | Number of nucleotides | Relationship with R1 reverse primer |
|---|---|---|---|
| M6-2 | 22 | 22 | Neither addition to nor deletion from 5' end<br>1 nucleotide is deleted from 3' end |
| TR | 23 | 18 | Neither addition to nor deletion from 5' end<br>5 nucleotides are deleted from 3' end |
| TR-2 | 24 | 18 | 2 nucleotides are deleted from 5' end<br>3 nucleotides are deleted from 3' end |

The positional relationship between the sequences of F1 forward primer and the variation primers thereof or R1 reverse primer and variation primers as mentioned above are shown in FIG. 4. Note that, the degree of positional shift in FIG. 4 indicates which direction and how long distance (in terms of the number of nucleotides) the 3'-end nucleotide of a variation primer shifted relative to the 3'-end nucleotide of the reference primer (F1 in the case of a forward primer, R1 in the case of a reverse primer). For example, since M1 forward primer is prepared by adding a single nucleotide to the 3' end of F1 forward primer, the degree of positional shift is represented by "+1". In contrast, in the case of MyTF-6 forward primer, which is prepared by deleting a single nucleotide from the 3' end of F1 forward primer, the degree of positional shift is represented by "−1".

All combinations of F1 forward primer and the variation primers thereof and R1 reverse primer and the variation primers thereof (see the following Table 4) were subjected to the multiplex real time quantitative PCR method of the present invention (see Example 2). At the reaction, *Mycoplasma genitalium* (about $10^6$ cfu/reaction) and *Lactobacillus bulgaricus* (about $10^6$ cfu/reaction) were used as bacteria; and a mixture of P1-1, P1-2, P1-3, P1-4 and P2 was used as the fluorescent probe. As the negative control, Distilled Water Deionized, Sterile (manufactured by Nippon Gene Co., Ltd.) was used.

TABLE 4

| Forward | F1 | | | | M1 | | | | TF | | | | MyTF-1 | | | |
|---|---|---|---|---|---|---|---|---|---|---|---|---|---|---|---|---|
| Reverse | M6-2 | TR | TR-2 | R1 | M6-2 | TR | TR-2 | R1 | M6-2 | TR | TR-2 | R1 | M6-2 | TR | TR-2 | R1 |
| Forward | MyTF-2 | | | | MyTF-3 | | | | MyTF-4 | | | | MyTF-5 | | | |
| Reverse | M6-2 | TR | TR-2 | R1 | M6-2 | TR | TR-2 | R1 | M6-2 | TR | TR-2 | R1 | M6-2 | TR | TR-2 | R1 |
| Forward | MyTF-6 | | | | | | | | | | | | | | | |
| Reverse | M6-2 | TR | TR-2 | R1 | | | | | | | | | | | | |

The detection results of samples in the multiplex real time quantitative PCR test are shown in FIG. 5. A case of "not detected" is expressed by "-". In the case of "detected", a ct value is shown. The ct value is the number of cycles repeated until the amount of a product amplified by PCR reached a predetermined value. The smaller ct value shows that a target is detected with a higher sensitivity. As is apparent from the results of FIG. 5, in the cases where forward primers M1, F1, TF, MyTF-1 and MyTF-5 were used, *Mycoplasma genitalium* was detected with high sensitivity and *Lactobacillus bulgaricus* (not *Mycoplasma*) was not detected, regardless of the type of the reverse primers (M6-2, TR, TR-2 or R1) used in combination. In contrast, in the cases where forward primers MyTF-3, MyTF-4 and MyTF-6 were used, if reverse primers M6-2, TR-2 and R1 were used in combination, *Lactobacillus bulgaricus* was not detected. However, if a reverse primer TR was used in combination, cross reactivity with *Lactobacillus bulgaricus* was observed. Note that, the ct value of MyTF-6 to *Lactobacillus bulgaricus* was relatively high (42.25) of the three forward primers MyTF-3, MyTF-4 and MyTF-6, meaning that the cross reactivity of MyTF-6 with *Lactobacillus bulgaricus* was lowest in these three. In the case where MyTF-2 forward primer was used, if M6-2 reverse primer was used in combination, *Lactobacillus bulgaricus* was not detected; however if TR, TR-2 and R1 were used in combination, the cross reactivity with *Lactobacillus bulgaricus* was observed.

From the results of FIG. 5, it was shown that F1, M1, TF, MyTF-1, MyTF-5 and MyTF-6 primers are preferable as the forward primer, in particular, F1 forward primer, MyTF-1 forward primer and MyTF-5 forward primer are more preferable.

INDUSTRIAL APPLICABILITY

According to the present invention, it is possible to provide a detection method for *Mycoplasma* by which a greater number of *Mycoplasma* species can be more quickly and easily detected with high sensitivity and accuracy and a set and kit of a forward primer, a reverse primer and a probe for the detection. The present invention can be used not only in detecting *Mycoplasma* contamination in sites of culturing cells in the fields of biological material-derived medicine, regenerative medicine and cell therapy but also in diagnosing e.g., infectious diseases with *Mycoplasma*.

The invention claimed is:

1. A kit for detecting *Mycoplasma* in a test sample by a multiplex real time quantitative PCR, wherein
the kit comprises one or more forward primers, two or more reverse primers, one or more probes and a solid support;
the probe(s) is immobilized onto the solid support;
the probe is a probe for specifically detecting products amplified by use of the forward primer and at least any one of the reverse primers;
the forward primer(s) is an oligonucleotide consisting of a nucleotide sequence, which is selected from the group consisting of nucleotide sequences each consisting of continuous 17 to 30 nucleotides in the nucleotide sequence of SEQ ID No: 1, and which contains a nucleotide sequence (caaggtatccs) at nucleotide positions 14 to 24 in SEQ ID No: 1; the reverse primers each are an oligonucleotide consisting of a nucleotide sequence, which is selected from the group consisting of nucleotide sequences each consisting of continuous 17 to 26 nucleotides in one or more nucleotide sequences of SEQ ID Nos: 14 and 17 to 20; and the probe(s) is an oligonucleotide, which consists of a nucleotide sequence selected from the group consisting of nucleotide sequences each consisting of continuous 17 to 26 nucleotides in the nucleotide sequence of SEQ ID No: 33, or which consists of a complementary nucleotide sequence thereto.

2. The kit according to claim 1, wherein the one or more forward primers are one or more oligonucleotides each consisting of a nucleotide sequence, which is selected from the group consisting of nucleotide sequences each consisting of continuous 17 to 30 nucleotides in the nucleotide sequence of SEQ ID No: 1, and which contains a nucleotide sequence (caaggtatccstac) at nucleotide positions 14 to 27 in SEQ ID No: 1.

3. The kit according to claim 1, wherein the one or more forward primers are two or more oligonucleotides and at least one of the oligonucleotides in said two or more oligonucleotides are selected from the following (A) and at least one of the oligonucleotides in said two or more oligonucleotides are selected from the following (B):
  (A) a forward primer, which is an oligonucleotide consisting of a nucleotide sequence, which is selected from the group consisting of nucleotide sequences each consisting of continuous 17 to 30 nucleotides in the nucleotide sequence of SEQ ID No: 2, and which contains a nucleotide sequence at nucleotide positions 14 to 24 in SEQ ID No: 2, and
  (B) a forward primer, which is an oligonucleotide consisting of a nucleotide sequence, which is selected from the group consisting of nucleotide sequences each consisting of continuous 17 to 30 nucleotides in the nucleotide sequence of SEQ ID No: 3, and which contains a nucleotide sequence at nucleotide positions 14 to 24 in SEQ ID No: 3.

4. The kit according to claim 1, containing two forward primers, wherein the two forward primers are an oligonucleotide consisting of any one nucleotide sequence selected from SEQ ID Nos: 4 to 7, 11 and 12, and an oligonucleotide consisting of the nucleotide sequence of SEQ ID No: 13.

5. The kit according to claim 1, wherein at least one of the reverse primers is an oligonucleotide containing a nucleotide sequence (wsccaaggcatccaccah) at nucleotide positions 3 to 20 in SEQ ID No: 14.

6. The kit according to claim 1, wherein the two or more reverse primers are two or more oligonucleotides selected from the following (C1), (C2-1), (C2-2), (C2-3), (D), (E1), (E2), (F) and (G):
  (C1) an oligonucleotide consisting of a nucleotide sequence selected from the group consisting of nucleotide sequences each consisting of continuous 17 to 26 nucleotides in the nucleotide sequence of SEQ ID No: 15,
  (C2-1) an oligonucleotide consisting of a nucleotide sequence selected from the group consisting of nucleotide sequences each consisting of continuous 17 to 26 nucleotides in the nucleotide sequence of SEQ ID No: 16 where m at nucleotide position 20 is a, and w at nucleotide position 22 is a,
  (C2-2) an oligonucleotide consisting of a nucleotide sequence selected from the group consisting of nucleotide sequences each consisting of continuous 17 to 26 nucleotides in the nucleotide sequence of SEQ ID No: 16 where m at nucleotide position 20 is c, and w at nucleotide position 22 is a,
  (C2-3) an oligonucleotide consisting of a nucleotide sequence selected from the group consisting of nucleotide sequences each consisting of continuous 17 to 26 nucleotides in the nucleotide sequence of SEQ ID No: 16 where m at nucleotide position 20 is a, and w at nucleotide position 22 is t,
  (D) an oligonucleotide consisting of a nucleotide sequence selected from the group consisting of nucleotide sequences each consisting of continuous 17 to 26 nucleotides in the nucleotide sequence of SEQ ID No:17,
  (E1) an oligonucleotide consisting of a nucleotide sequence selected from the group consisting of nucleotide sequences each consisting of continuous 17 to 24 nucleotides in the nucleotide sequence of SEQ ID No: 18 where s at nucleotide position 2 is g, and r at each of nucleotide positions 4 and 9 is g,
  (E2) an oligonucleotide consisting of a nucleotide sequence selected from the group consisting of nucleotide sequences each consisting of continuous 17 to 24 nucleotides in the nucleotide sequence of SEQ ID No: 18 where s at nucleotide position 2 is c, and r at each of nucleotide positions 4 and 9 is a,
  (F) an oligonucleotide consisting of a nucleotide sequence selected from the group consisting of nucleotide sequences each consisting of continuous 17 to 25 nucleotides in the nucleotide sequence of SEQ ID No: 19, and
  (G) an oligonucleotide consisting of a nucleotide sequence selected from the group consisting of nucleotide sequences each consisting of continuous 17 to 23 nucleotides in the nucleotide sequence of SEQ ID No: 20.

7. The kit according to claim 1, wherein the two or more reverse primers are two or more oligonucleotides selected from the following oligonucleotides:
  an oligonucleotide consisting of the nucleotide sequence of SEQ ID No: 21,
  an oligonucleotide consisting of the nucleotide sequence of SEQ ID No: 22,
  an oligonucleotide consisting of the nucleotide sequence of SEQ ID No: 24,
  an oligonucleotide consisting of the nucleotide sequence of SEQ ID No: 25,
  an oligonucleotide consisting of the nucleotide sequence of SEQ ID No: 26,
  an oligonucleotide consisting of the nucleotide sequence of SEQ ID No: 27,
  an oligonucleotide consisting of the nucleotide sequence of SEQ ID No: 17,
  an oligonucleotide consisting of the nucleotide sequence of SEQ ID No: 28,
  an oligonucleotide consisting of the nucleotide sequence of SEQ ID No: 29,
  an oligonucleotide consisting of the nucleotide sequence of SEQ ID No: 19, and
  an oligonucleotide consisting of the nucleotide sequence of SEQ ID No: 20.

8. The kit according to claim 1, wherein the probe is an oligonucleotide containing a nucleotide sequence (sggrtggaty) at nucleotide positions 7 to 16 in SEQ ID No: 33 or a complementary nucleotide sequence thereto.

9. The kit according to claim 1, wherein the one or more probes are one or more oligonucleotides selected from the following (H) to (L):
   (H) an oligonucleotide, which consists of a nucleotide sequence selected from the group consisting of nucleotide sequences each consisting of continuous 17 to 26nucleotides in the nucleotide sequence of SEQ ID No: 34, or which consists of a complementary nucleotide sequence thereto,
   (I) an oligonucleotide, which consists of a nucleotide sequence selected from the group consisting of nucleotide sequences each consisting of continuous 17 to 26nucleotides in the nucleotide sequence of SEQ ID No: 35, or which consists of a complementary nucleotide sequence thereto,
   (J) an oligonucleotide, which consists of a nucleotide sequence selected from the group consisting of nucleotide sequences each consisting of continuous 17 to 26nucleotides in the nucleotide sequence of SEQ ID No: 36, or which consists of a complementary nucleotide sequence thereto,
   K) an oligonucleotide, which consists of a nucleotide sequence selected from the group consisting of nucleotide sequences each consisting of continuous 17 to 26nucleotides in the nucleotide sequence of SEQ ID No: 37, or which consists of a complementary nucleotide sequence thereto, and
   (L) an oligonucleotide, which consists of a nucleotide sequence selected from the group consisting of nucleotide sequences each consisting of continuous 17 to 26 nucleotides in the nucleotide sequence of SEQ ID No: 38, or which consists of a complementary nucleotide sequence thereto.

10. The kit according to claim 1, wherein the one or more probes are one or more oligonucleotides selected from the following (h) to (l):
   (h) an oligonucleotide consisting of the nucleotide sequence of SEQ ID No: 39,
   (i) an oligonucleotide consisting of the nucleotide sequence of SEQ ID No: 40,
   (j) an oligonucleotide consisting of the nucleotide sequence of SEQ ID No: 41,
   (k) an oligonucleotide consisting of the nucleotide sequence of SEQ ID No: 42, and
   (l) an oligonucleotide consisting of the nucleotide sequence of SEQ ID No: 43.

11. A set of a forward primer, a reverse primer and a probe for detecting *Mycoplasma* in a test sample by a multiplex real time quantitative PCR, wherein the set contains one or more forward primers, two or more reverse primers and one or more probes;
   the probe(s) is a probe for specifically detecting products amplified by use of the forward primer and at least any one of the reverse primers and the probe is labeled with a fluorescent substance;
   the forward primer(s) is an oligonucleotide consisting of a nucleotide sequence, which is selected from the group consisting of nucleotide sequences each consisting of continuous 17 to 30 nucleotides in the nucleotide sequence of SEQ ID No: 1, and which contains a nucleotide sequence (caaggtatccs) at nucleotide positions 14 to 24 in SEQ ID No: 1; the reverse primers each are an oligonucleotide consisting of a nucleotide sequence, which is selected from the group consisting of nucleotide sequences each consisting of continuous 17 to 26 nucleotides in one or more nucleotide sequences of SEQ ID Nos: 14 and 17 to 20; and the probe(s) is an oligonucleotide, which consists of a nucleotide sequence selected from the group consisting of nucleotide sequences each consisting of continuous 17 to 26 nucleotides in the nucleotide sequence of SEQ ID No: 33, or which consists of a complementary nucleotide sequence thereto.

12. A method for detecting *Mycoplasma* in a test sample by a multiplex real time quantitative PCR, comprising
   (a) Step a of extracting DNA from the test sample,
   (b) Step b of performing a multiplex real time quantitative PCR using the DNA extracted in Step a as a template, and one of more forward primers and two or more reverse primers, and
   (c) Step c of detecting the presence of *Mycoplasma* in the test sample by detecting a product amplified by the multiplex real time quantitative PCR in Step b by use of one or more probes;
   the probe(s) is a probe for specifically detecting products amplified by use of the forward primer and at least any one of the reverse primers;
   the forward primer(s) is an oligonucleotide consisting of a nucleotide sequence, which is selected from the group consisting of nucleotide sequences each consisting of continuous 17 to 30 nucleotides in the nucleotide sequence of SEQ ID No: 1, and which contains a nucleotide sequence (caaggtatccs) at nucleotide positions 14 to 24 in SEQ ID No: 1; the reverse primers each are an oligonucleotide consisting of a nucleotide sequence, which is selected from the group consisting of nucleotide sequences each consisting of continuous 17 to 26 nucleotides in one or more nucleotide sequences of SEQ ID Nos: 14 and 17 to 20; and the probe(s) is an oligonucleotide, which consists of a nucleotide sequence selected from the group consisting of nucleotide sequences each consisting of continuous 17 to 26 nucleotides in the nucleotide sequence of SEQ ID No: 33, or which consists of a complementary nucleotide sequence thereto.

13. The method for detecting *Mycoplasma* according to claim 12, wherein the product amplified by the multiplex real time quantitative PCR in Step c is detected by detecting whether or not a specific hybridization with the probe as defined in claim 12 occurs.

14. The method for detecting *Mycoplasma* according to claim 12, wherein the detection limit in sensitivity of one or more *Mycoplasma* species selected from the group consisting of *Mycoplasma arginini, Mycoplasma buccale, Mycoplasma faucium, Mycoplasma hominis, Mycoplasma orale, Mycoplasma salivarium, Mycoplasma fermentans, Mycoplasma lipophilum, Mycoplasma primatum, Mycoplasma hyorhinis, Mycoplasma synoviae, Mycoplasma genitalium, Mycoplasma pneumoniae, Acholeplasma laidlawii, Ureaplasma urealyticum, Mycoplasma gallisepticum* and *Spiroplasma citri*, is 10 cfu/mL or less.

* * * * *